(12) United States Patent
Bullinga

(10) Patent No.: US 9,795,315 B2
(45) Date of Patent: Oct. 24, 2017

(54) CATHETER SYSTEM FOR MAPPING OF THE LEFT ATRIUM, RIGHT ATRIUM AND CORONARY SINUS

(71) Applicant: John Bullinga, Philadelphia, PA (US)

(72) Inventor: John Bullinga, Philadelphia, PA (US)

( * ) Notice: Subject to any disclaimer, the term of this patent is extended or adjusted under 35 U.S.C. 154(b) by 111 days.

(21) Appl. No.: 14/166,480

(22) Filed: Jan. 28, 2014

(65) Prior Publication Data

US 2015/0208937 A1    Jul. 30, 2015

(51) Int. Cl.
| | |
|---|---|
| *A61B 5/05* | (2006.01) |
| *A61B 5/0408* | (2006.01) |
| *A61B 5/00* | (2006.01) |
| *A61B 5/042* | (2006.01) |
| *A61B 5/06* | (2006.01) |

(52) U.S. Cl.
CPC .......... *A61B 5/0408* (2013.01); *A61B 5/0044* (2013.01); *A61B 5/0422* (2013.01); *A61B 5/6856* (2013.01); *A61B 5/6886* (2013.01); *A61B 5/062* (2013.01)

(58) Field of Classification Search
USPC ....................................................... 600/424
See application file for complete search history.

(56) References Cited

U.S. PATENT DOCUMENTS

| | | | | |
|---|---|---|---|---|
| 5,239,999 | A * | 8/1993 | Imran | A61B 5/0422 600/374 |
| 5,772,590 | A | 6/1998 | Webster, Jr. | |
| 5,873,865 | A | 2/1999 | Horzewski et al. | |
| 5,997,526 | A * | 12/1999 | Giba | A61M 25/0041 600/373 |
| 6,096,053 | A | 8/2000 | Bates | |
| 6,738,655 | B1 | 5/2004 | Sen et al. | |
| 8,346,339 | B2 | 1/2013 | Kordis et al. | |
| 2003/0078494 | A1 * | 4/2003 | Panescu | A61B 34/20 600/424 |
| 2005/0033135 | A1 * | 2/2005 | Govari | A61B 5/053 600/374 |
| 2006/0089637 | A1 * | 4/2006 | Werneth | A61B 18/1492 606/41 |
| 2007/0167801 | A1 * | 7/2007 | Webler | G06F 19/3437 600/459 |
| 2008/0058834 | A1 | 3/2008 | Cheng et al. | |

(Continued)

*Primary Examiner* — Joel F Brutus
(74) *Attorney, Agent, or Firm* — Fay Kaplun & Marcin, LLP

(57) ABSTRACT

A pair of new catheters designed to be deployed as a catheter system to allow a simultaneous acquisition of electrograms from widely dispersed electrodes in the left atrium, right atrium, and coronary sinus. The first catheter is the spiral globe catheter which has the primary shape of a spiral globe and has additional modifications to facilitate safe entry into the left atrium, to orient the primary axis of the spiral globe toward the mitral valve, and to maximize contact of electrodes to multiple areas of the left atrium. The second catheter is the right atrial and coronary sinus catheter (RA-CS catheter) which allows for electrogram acquisition from the length of the coronary sinus and dispersed areas of the right atrium. The catheter system is designed to provide adequate electrode sensor information so that panoramic mapping of the both atria and the coronary sinus may be performed.

26 Claims, 27 Drawing Sheets

(56) References Cited

U.S. PATENT DOCUMENTS

| | | | |
|---|---|---|---|
| 2008/0281312 A1* | 11/2008 | Werneth | A61B 18/1492 606/33 |
| 2009/0198226 A1 | 8/2009 | Prakash et al. | |
| 2010/0094274 A1 | 4/2010 | Narayan et al. | |
| 2011/0251505 A1 | 10/2011 | Narayan et al. | |
| 2011/0257723 A1* | 10/2011 | McNamara | A61B 17/0057 623/1.11 |
| 2013/0085360 A1 | 4/2013 | Grunewald et al. | |

* cited by examiner

RA-CS Catheter
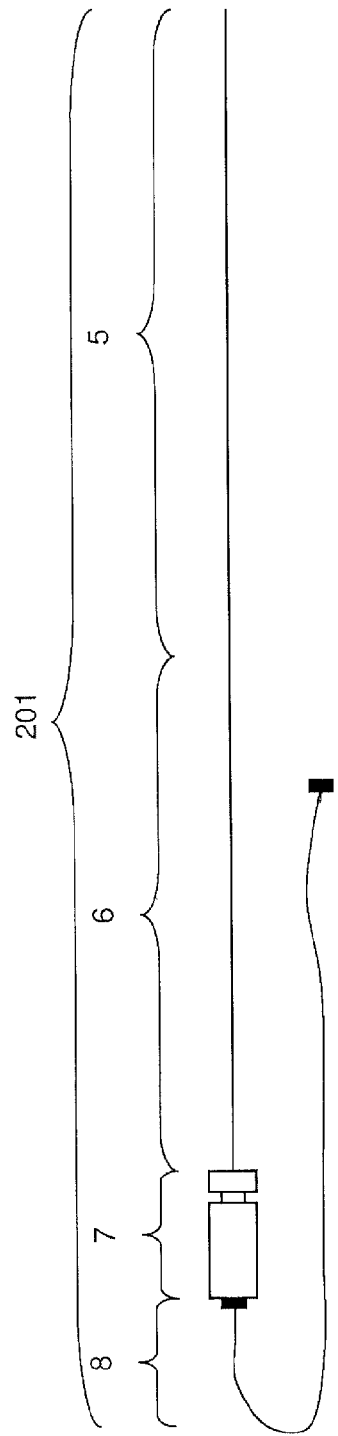
FIG. 3A: RA-CS Catheter without Distal Curl Applied
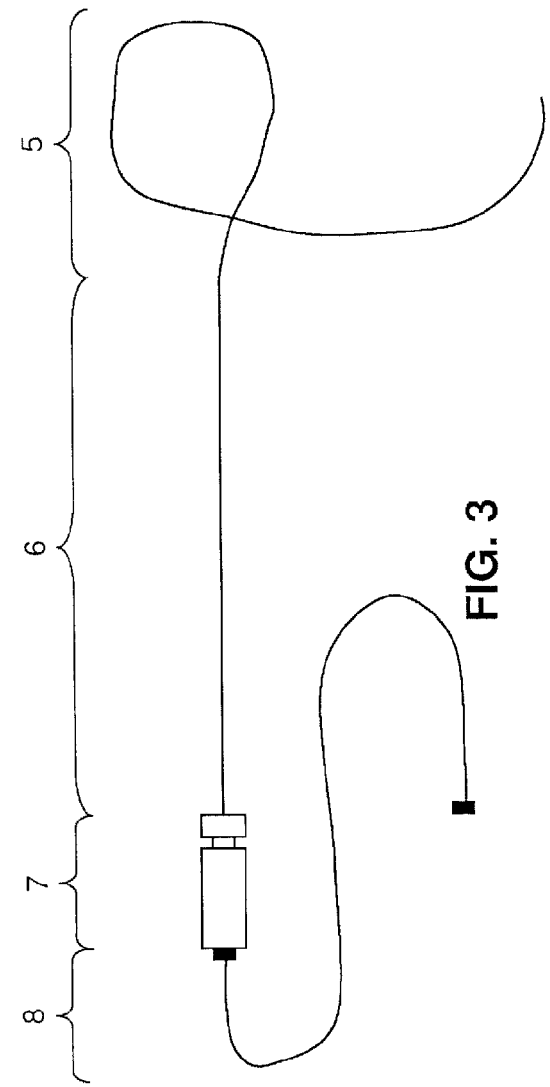
FIG. 3B: RA-CS Catheter with Distal Portion Anatomically Curved
FIG. 3

Regions of Spiral Globe Catheter Portion '1', Cranial View

Views of Spiral Globe Catheter Portion 1
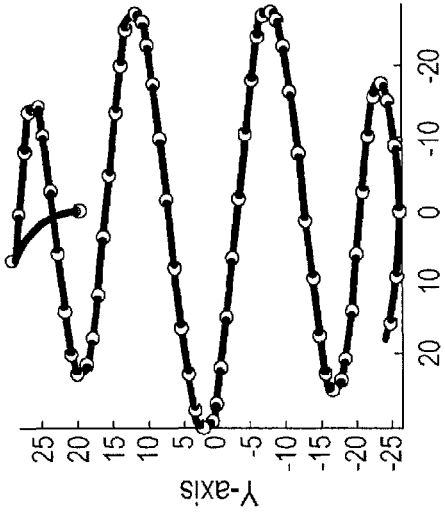
FIG. 6A: Right Superior
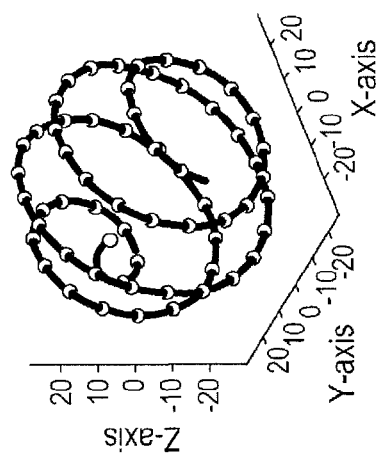
FIG. 6B: Cranial
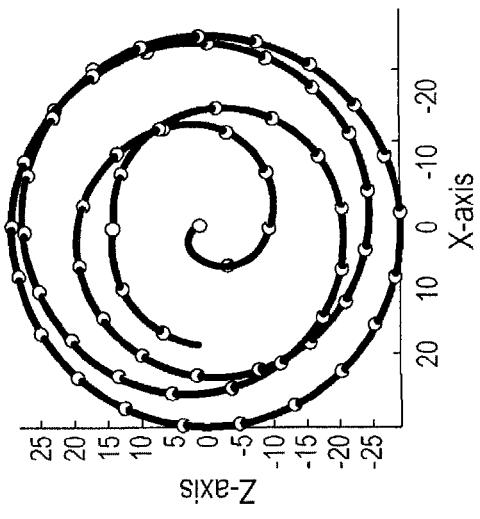
FIG. 6C: Left Anterior Oblique
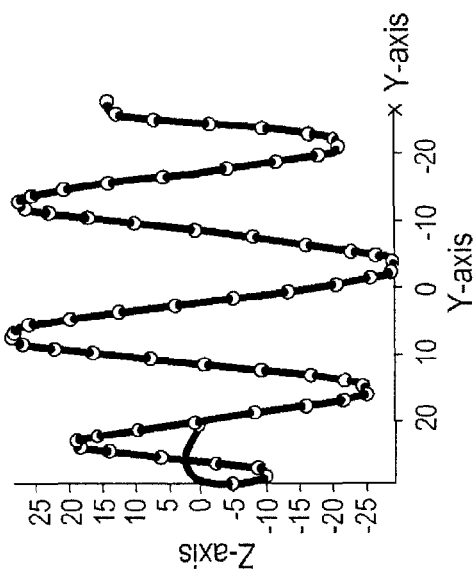
FIG. 6D: Right Anterior Oblique
FIG. 6

Spiral Globe Electrode Sensor Relationships
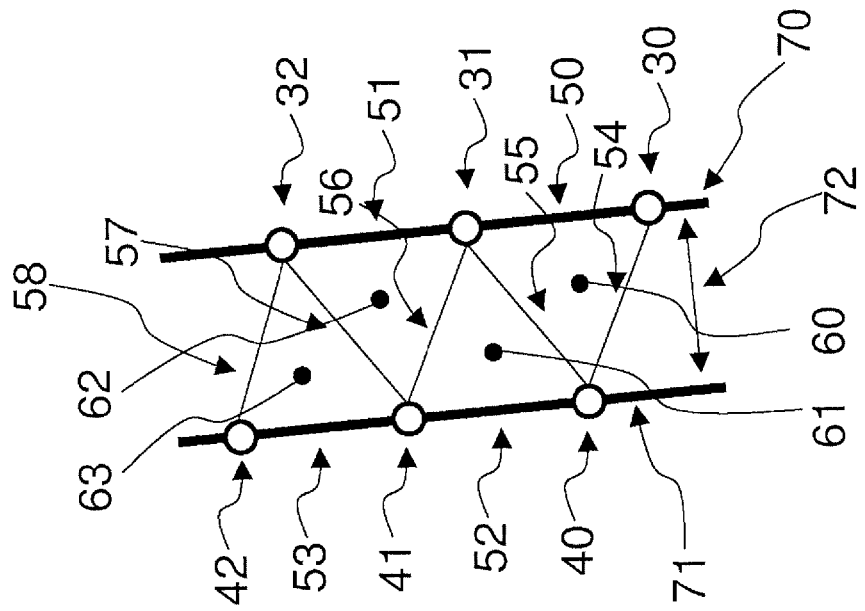
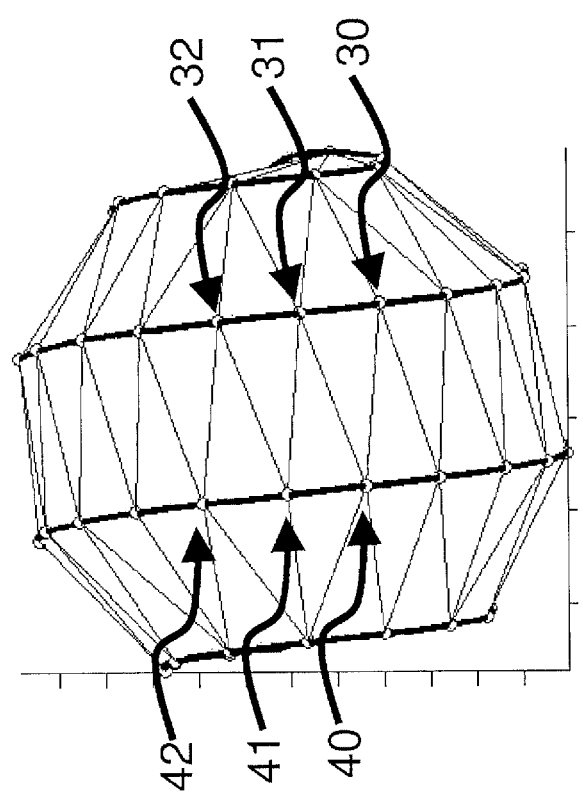
FIG. 7A Left Posterior Oblique
FIG. 7B Segment from Left Posterior Oblique
FIG. 7

Spiral Globe Electrode Sensors: Triangular Faces
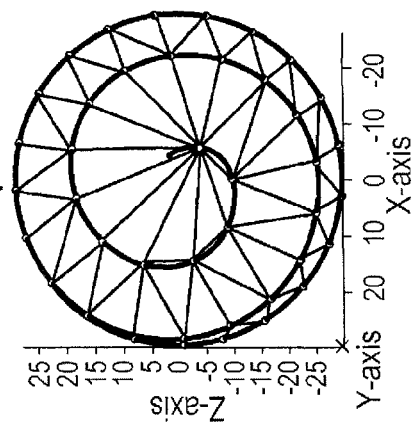
FIG. 8A: Right Superior
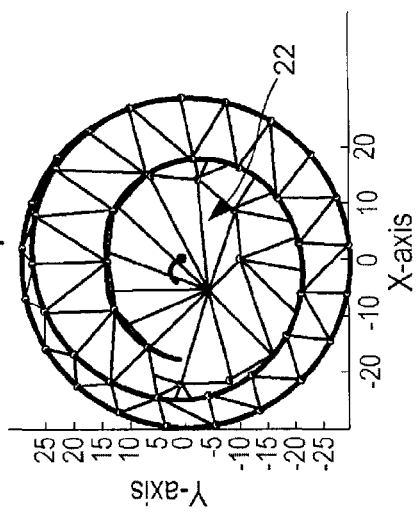
FIG. 8B: Left Anterior Oblique
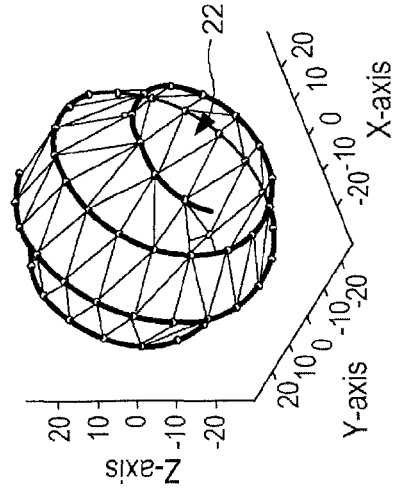
FIG. 8C: Right Posterior Oblique
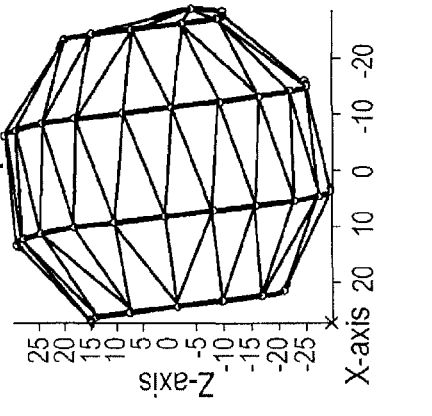
FIG. 8D: Right Anterior Oblique
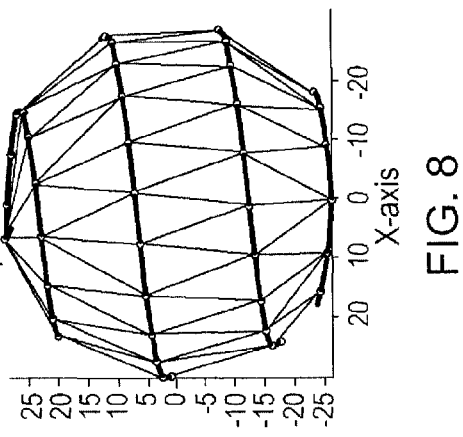
FIG. 8E: Superior Spiral Globe
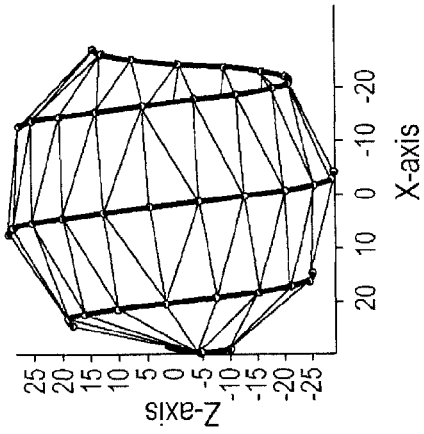
FIG. 8F: Left Posterior Oblique
FIG. 8

FIG. 9A: Right Anterior Oblique View    FIG. 9B: Left Anterior Oblique View

FIG. 10A: Right Anterior Oblique View    FIG. 10B: Left Anterior Oblique View

FIG. 11A: Right Anterior Oblique View    FIG. 11B: Left Anterior Oblique View

FIG. 12A: Right Anterior Oblique View    FIG. 12B: Left Anterior Oblique View

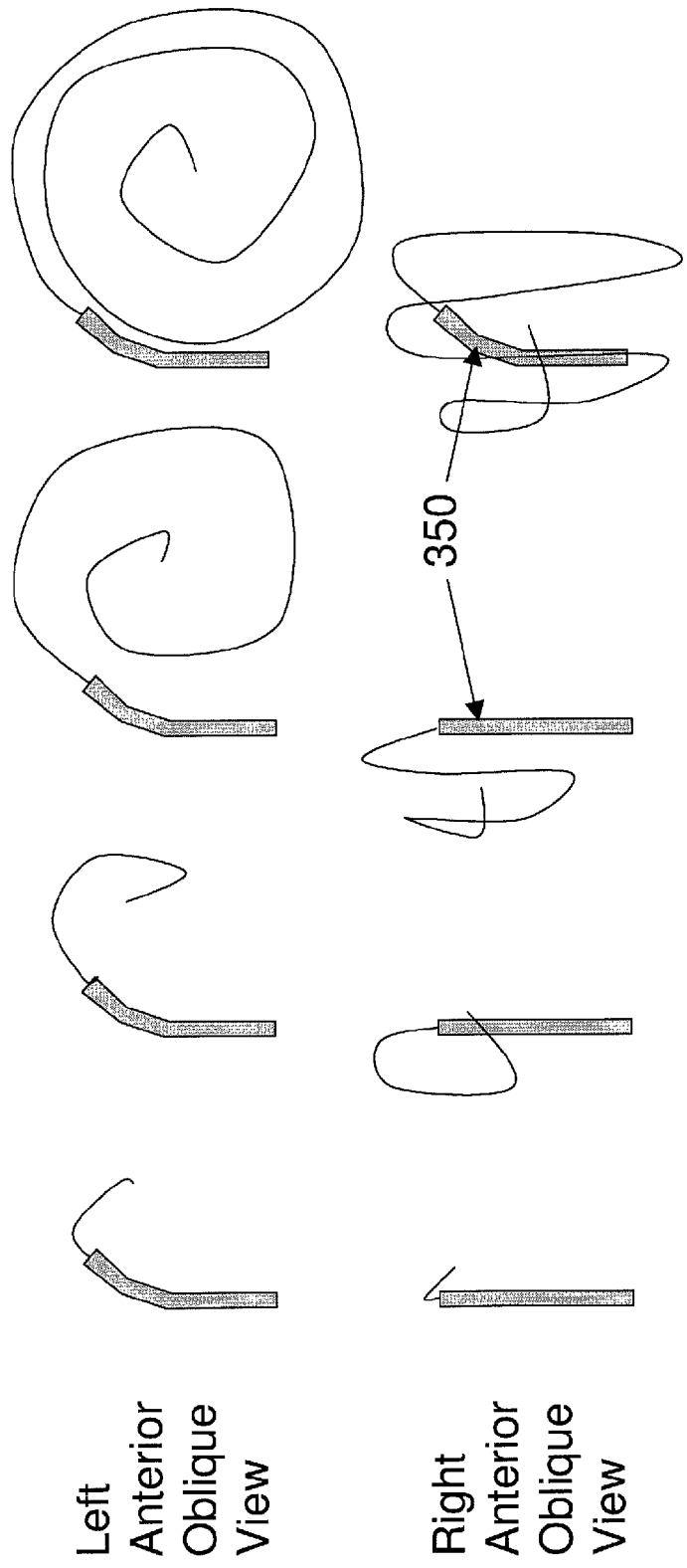

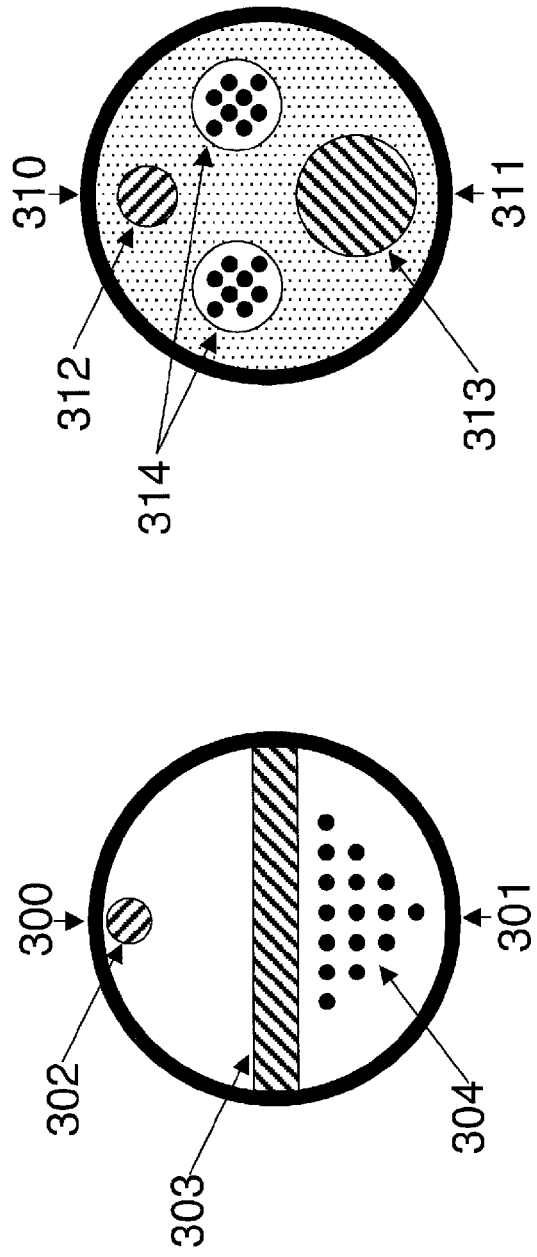

Multiple Parameter Examples and Solutions to A Spiral Globe Fitting Those Parameters
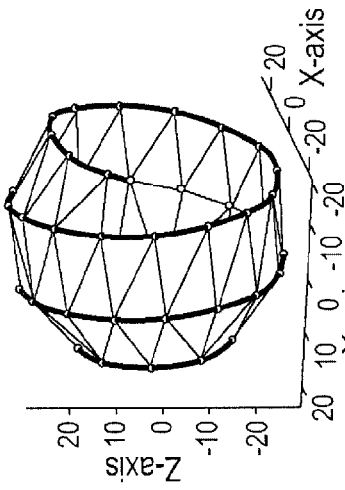
FIG. 15A
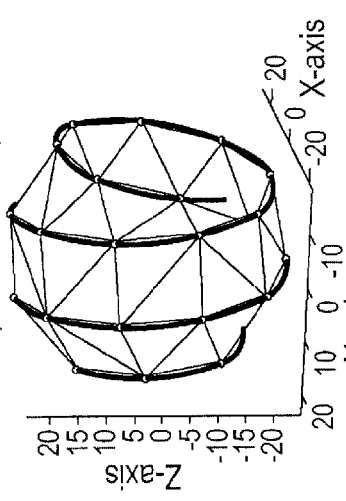
FIG. 15B
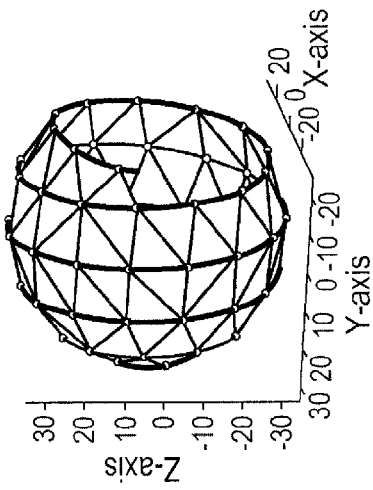
FIG. 15C
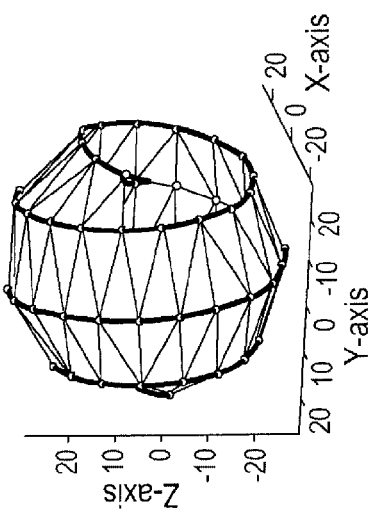
FIG. 15D
FIG. 15

Helix Catheter
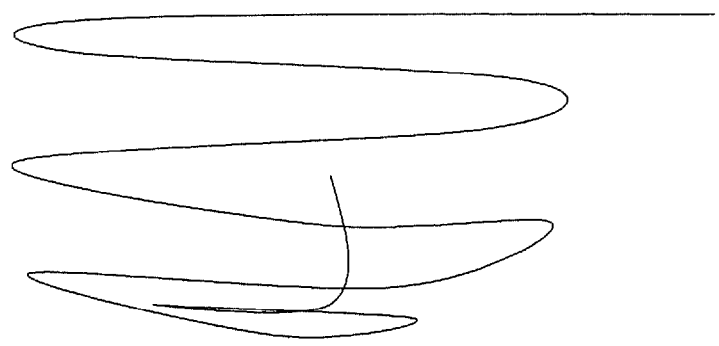
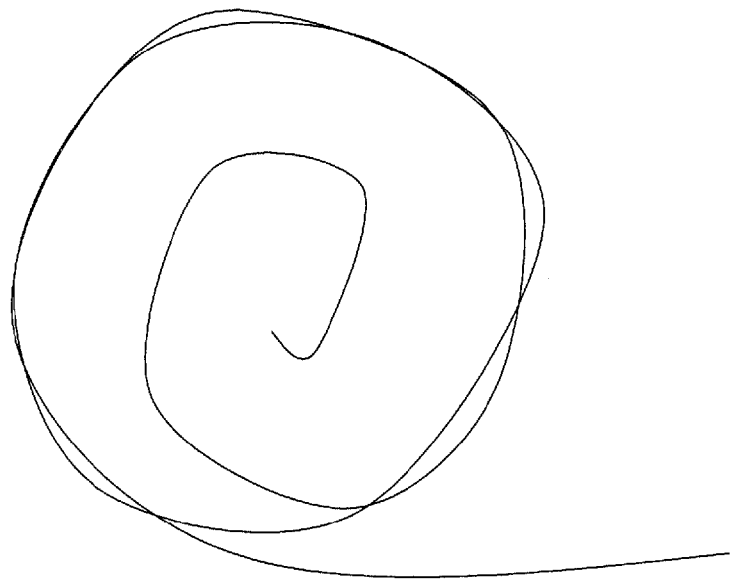
FIG. 16A: Left Anterior Oblique View    FIG. 16B: Right Anterior Oblique View
FIG. 16

Conical Helix Catheter:
Two curves, tip and prime, cone shaped, no mitral valve reorientation, no actuator, expands as introduced into atrium FIG. 17A: Left Anterior Oblique View    FIG. 17B: Right Anterior Oblique View Hemisphere Spiral Catheter FIG. 18A: Left Anterior Oblique View    FIG. 18B: Right Anterior Oblique View FIG. 19A: Left Anterior Oblique View    FIG. 19B: Right Anterior Oblique View FIG. 20A: Left Anterior Oblique View   FIG. 20B: Right Anterior Oblique View FIG. 21: Left Anterior Oblique View Duo-Spiral Globe Catheter with Connected Tips

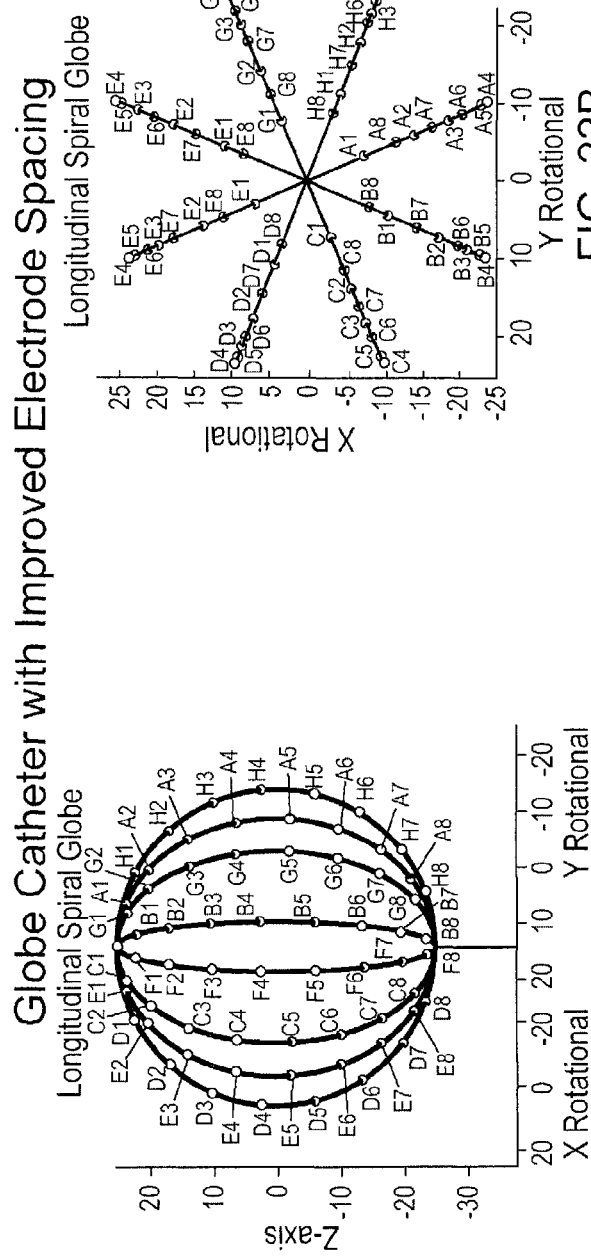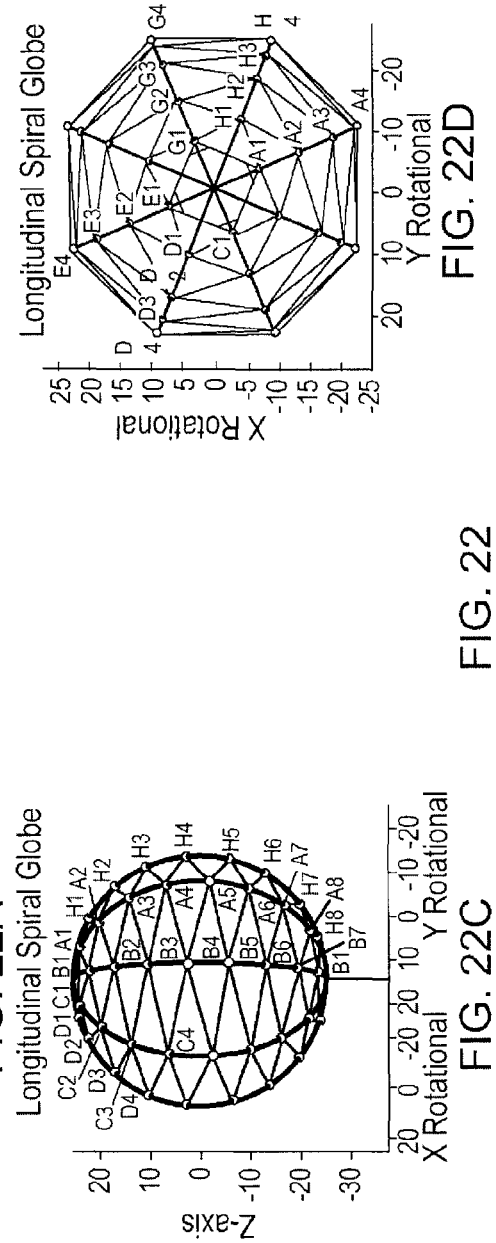
FIG. 22

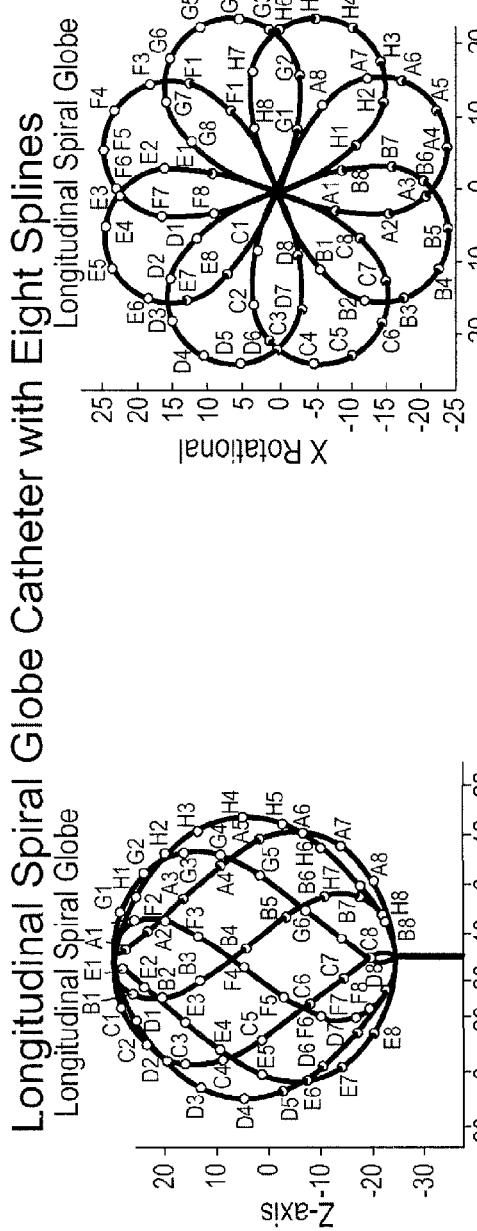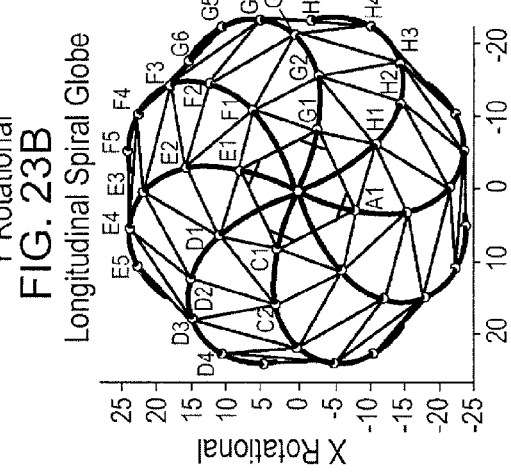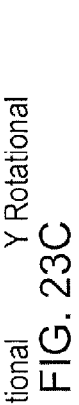
FIG. 23

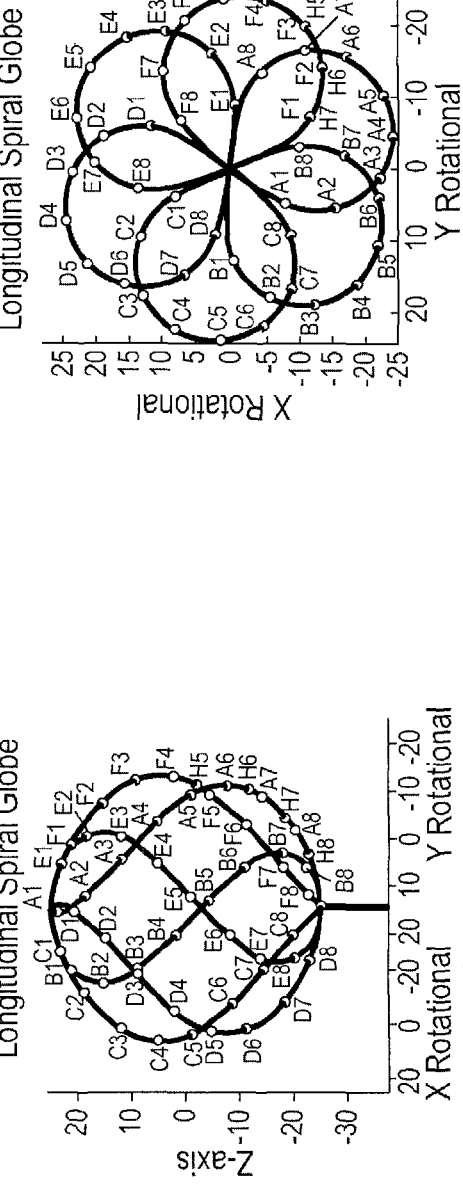
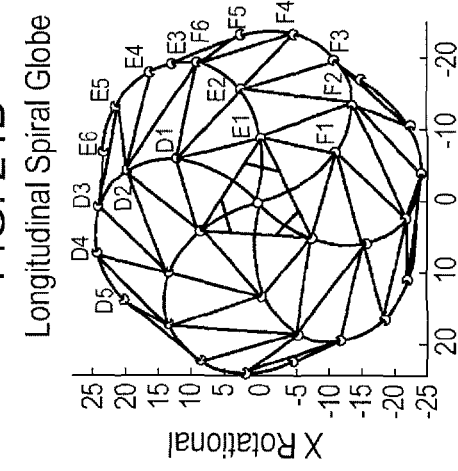
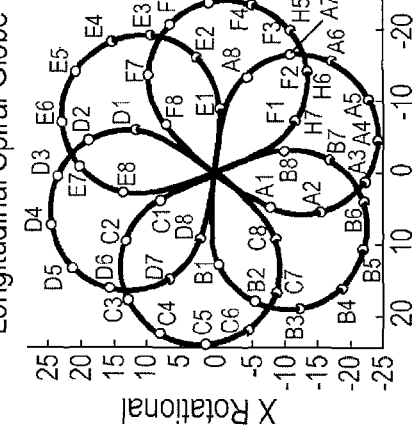
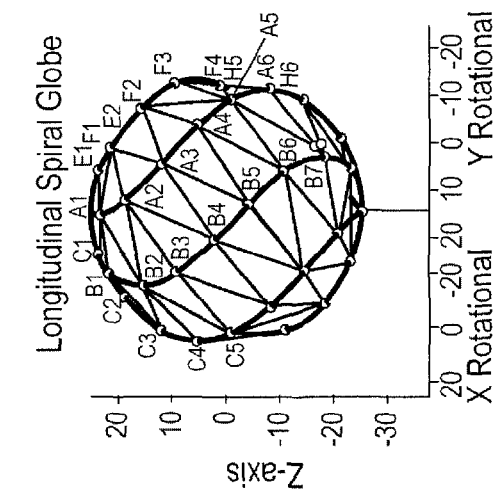
FIG. 24A
FIG. 24B
FIG. 24C
FIG. 24D
FIG. 24

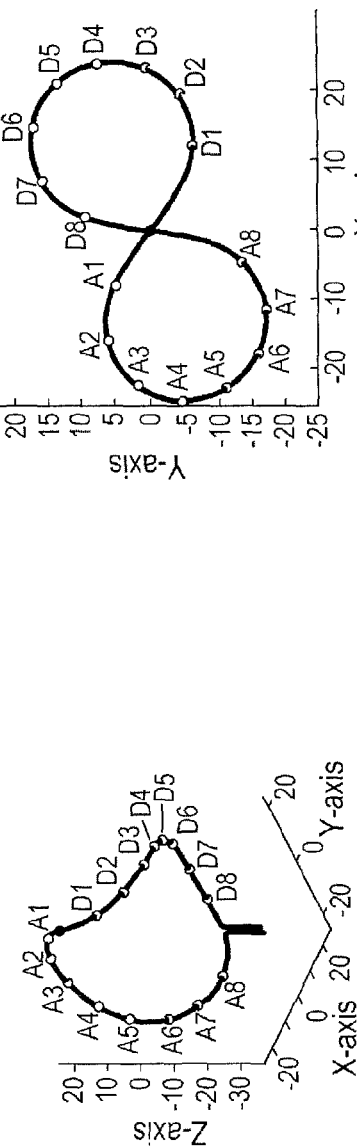
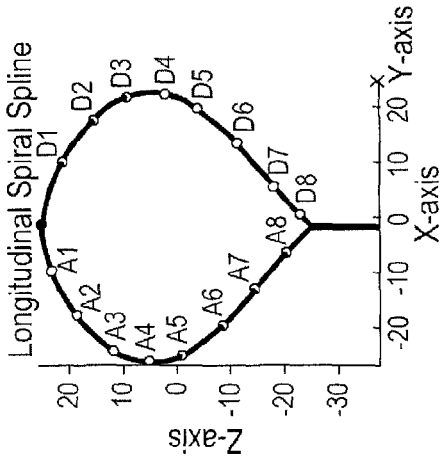
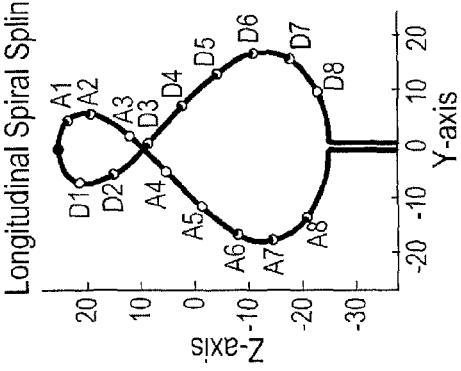
FIG. 25A
FIG. 25B
FIG. 25C
FIG. 25D
FIG. 25

Longitudinal Spiral Globe Wire for Spline and Electrodes

FIG. 26A: Tip Portion

FIG. 26B: Proximal Portion

Catheter System:
Longitudinal Spiral Globe Catheter and the RA-CS Catheter

CATHETER SYSTEM FOR MAPPING OF THE LEFT ATRIUM, RIGHT ATRIUM AND CORONARY SINUS

BACKGROUND

Atrial fibrillation is the most common sustained arrhythmia and has an increasing incidence and prevalence in the United States and worldwide. Catheter ablation of atrial fibrillation is potentially curative and has become a common procedure. A cornerstone of catheter ablation of atrial fibrillation is isolation of the pulmonary veins according to current guidelines (Heart Rhythm. 2012; 9(4):632-696). Pulmonary vein isolation alone has a high incidence of recurrent atrial fibrillation (Circulation. 2003; 108:2355-2360). Identification of additional regions of the atrium to treat with ablation are difficult to determine and controversial.

Additional regions may include linear ablation (Circulation. 2004; 110:2996-3002) and ablation of complex fractionated atrial electrograms (J Am Coll Cardiol. 2004; 43:2044-53).

Three-dimensional mapping of arrhythmias is commonly performed to identify the mechanisms of an arrhythmia and to facilitate targeted ablation of the arrhythmia. Mapping of stable arrhythmias is commonly performed. Atrial fibrillation is an unstable arrhythmia making traditional point-by-point activation mapping not possible. Sources and mechanisms of atrial fibrillation are controversial and in theory include multi-wavelet reentry (Moe G K, Abildskov A J: Am H J. 1959: 59-70), focal sources of electrical activity (Haïssaguerre M, et. al.: N Engl J Med 1998; 339:659-66), and spiral waves (rotors) of electrical activity (Skanes, et. al.: Circulation, 1998; 98(12):1236-1248). In order to effectively create a map to identify the mechanisms of atrial fibrillation, a catheter or catheter system that has a widely dispersed set of electrode sensors is required to acquire simultaneous signals from disperse areas of the atrium. Ablation of atrial fibrillation seeks to disrupt the mechanisms of atrial fibrillation to facilitate restoration of sinus rhythm. Currently, techniques that attempt to determine the sources and mechanisms of atrial fibrillation are inadequate due to a limited distribution of electrode sensors in the atrium to fully define the mechanism of atrial fibrillation.

Existing catheter designs for collecting electrograms include basket shaped catheter designs. One example of a basket catheter design is the Constellation catheter (Boston Scientific, Natick, Mass., USA). This design partially fulfills the need of a large number of contact electrodes to cover a large area of the one of the two atria. This design is limited by being expensive to manufacture, having limited coverage with electrodes at the proximal and distal poles, having limited contact to multiple areas in the atrium, being difficult to estimate size relative to the atrium, and that the size is not adjustable. When deployed in the left atrium, there is minimal contact with the interatrial septum and regions close to the right pulmonary veins.

DESCRIPTION OF THE DRAWINGS

FIG. 3A shows the right atrial-coronary sinus catheter ("RA-CS catheter") that comprises a distal recording portion 5, shaft portion 6, handle portion with an actuator 7, and a connecting cable portion 8.

FIG. 3B shows the RA-CS catheter, when positioned in the right atrium and coronary sinus, having the distal recording portion curved using the actuator as depicted in FIG. 3B.

FIG. 6A shows the same model of the spiral globe portion of the catheter as FIG. 5 projected to a right superior view.

FIG. 6B shows the same model of the spiral globe portion of the catheter as FIG. 5 projected to a cranial view.

FIG. 6C shows the same model of the spiral globe portion of the catheter as FIG. 5 projected to a left anterior oblique view.

FIG. 6D shows the same model of the spiral globe portion of the catheter as FIG. 5 projected to a right anterior oblique view.

FIG. 7A shows the same model of the spiral globe portion of the catheter as FIG. 5 with exemplary sensor electrodes labeled 30, 31, 32, 40, 41, 42.

FIG. 7B shows the same exemplary sensor electrodes 30, 31, 32, 40, 41, 42 as FIG. 7A which are used to form triangular mesh which represents the surface of the spiral globe. The edges of the triangles along the shaft of the catheter are labeled 50, 51, 52, and 53. The edges between electrode sensors on separate loops of the spiral globe which form the minimum distance triangles are labeled 54, 55, 56, 57, and 58. These edges 50 through 58 form the triangles 60, 61, 62, and 63. Regionally, the catheter may be viewed as having separate loops of the spiral globe are labeled 70 and 71, which are actually part of one continuous spiral. The distance between loops 70 and 71 is labeled as 72.

FIGS. 8A-F show the same model of the spiral globe portions of the catheter as FIGS. 5-7 with the resultant triangular mesh depicted in multiple orthogonal views. The triangular mesh encloses all portions of the spiral globe except for the mitral valve portion 22, which is depicted in FIG. 8A and FIG. 8B.

FIG. 9A shows a right anterior oblique view and FIG. 9B shows a left anterior oblique view of the spiral globe catheter relative to the approximate left atrial anatomy.

FIGS. 13A-D shows introduction of the spiral globe catheter into the left atrium and how sequential loops of the catheter change the orientation of the catheter tip and body relative to the left atrium for final positioning.

FIG. 14A shows a cross-section view of the spiral globe catheter using a metal bar as a catheter shape stabilizer.

FIG. 14B shows a cross-section view of the spiral globe catheter using a nitinol filament to maintain the shape of the spiral globe.

FIGS. 15A-D shows an exemplary spiral globe catheters with varying parameter sets.

FIGS. 16A-B shows an exemplary helix catheter. The body portion of the catheter may also be described as being a spiral around a cylinder with geometric progression of sequential loops.

FIG. 21 shows the catheter in a position with an additional one half loop or 180 degree rotation of the duo-spiral globe with the single shaft element extending into the atrium.

FIG. 22 shows a globe catheter improved electrode spacing and with eight splines. FIG. 22A show the catheter from a lateral view and FIG. 22B from a superior view. FIG. 22C shows a lateral view with triangles where the electrodes are the vertices of the triangles. FIG. 22D shows a superior view with triangles where the electrodes are the vertices of the triangles.

FIG. 23 shows a longitudinal spiral globe catheter with eight splines. FIG. 23A show the catheter from a lateral view and FIG. 23B from a superior view. FIG. 23C shows a lateral view with triangles where the electrodes are the vertices of the triangles. FIG. 23D shows a superior view with triangles where the electrodes are the vertices of the triangles.

FIG. 24 shows a longitudinal spiral globe catheter with six splines. FIG. 24A show the catheter from a lateral view and FIG. 24B from a superior view. FIG. 24C shows a lateral view with triangles where the electrodes are the vertices of the triangles. FIG. 24D shows a superior view with triangles where the electrodes are the vertices of the triangles.

FIG. 25 shows a preshaped wire which produces the two splines 'A' and 'D' of the longitudinal spiral globe shown in FIG. 24. FIG. 25A shows the catheter from a superior oblique view and FIG. 25B from a superior view. FIG. 25C shows a lateral Y-Z plane view and FIG. 25D shows a lateral X-Z plane view of the splines. FIG. 24 has six splines labeled A, B, C, D, E and F. Splines A, C and E are the 'odd splines' and splines B, D and F are the 'even splines'. FIG. 25 shows an 'odd' spline A and an 'even' spline D as being on one continuous preshaped wire. Electrodes on spline 'A' are labeled A1, A2, A3, A4, A5, A6, A7 and A8. Electrodes on spline 'D' are labeled D1, D2, D3, D4, D5, D6, D7 and D8.

DETAILED DESCRIPTION

Figure 1:
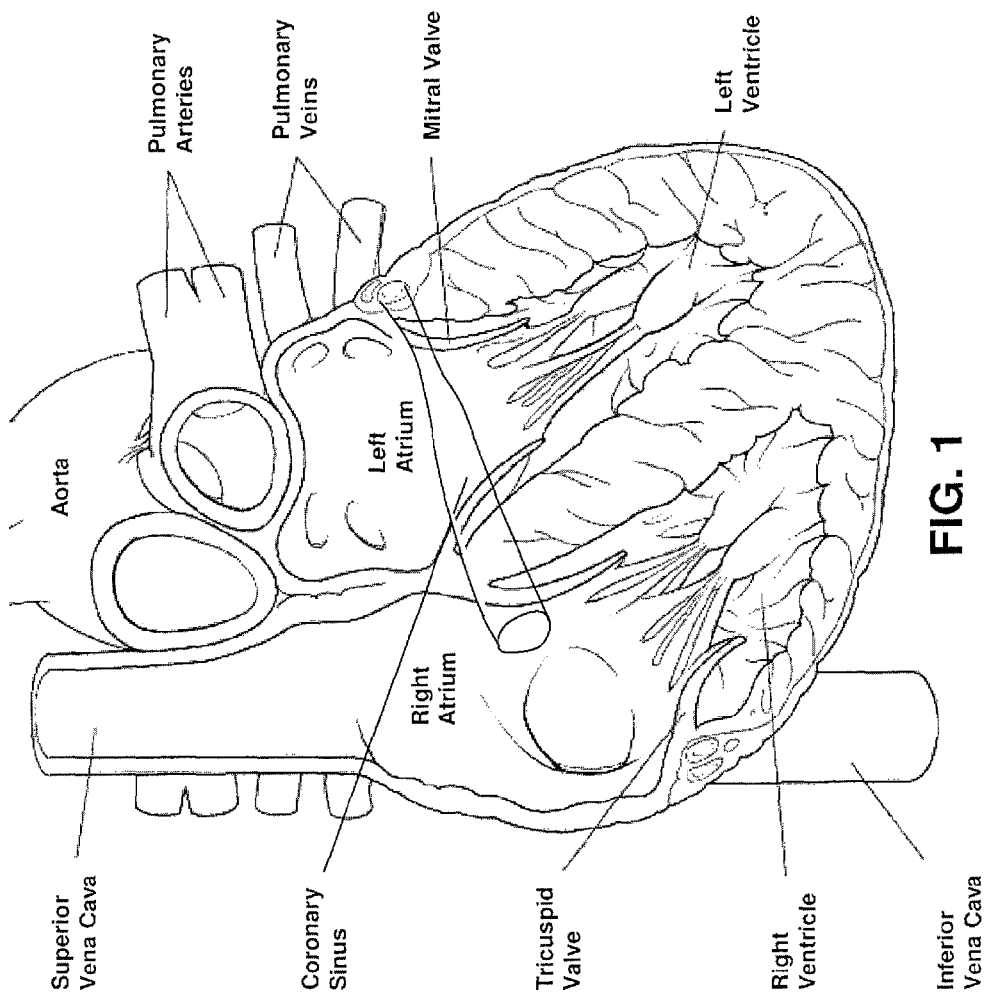
FIG. 1 shows a diagram of the left atrium, right atrium and coronary sinus in spatial relation to the other chambers and structures of the heart including the right ventricle, left ventricle, inferior vena cava, superior vena cava and mitral valve.

Embodiments of the presently disclosed medical devices are described in detail with reference to the drawings, in which like reference numerals identify corresponding elements in multiple views. As used herein, the term "distal" refers to the component of the medical device furthest from the user while the term "proximal" refers to the component of the medical device closest to the user.

The described catheter system is intended to be used with an electrophysiology recording system and a three-dimensional mapping system. The catheter system is designed to provide adequate electrode sensor information from a plurality of spatially dispersed locations so that panoramic mapping of the both atria and the coronary sinus may be performed. The exemplary embodiments include a first electrophysiology catheter having a preshaped spiral globe geometry designed to conform to the shape of the left atrium and having electrodes spaced along the length of the distal portion of the catheter. The exemplary embodiments further include a second electrophysiology catheter designed to conform to the right atrium and coronary sinus with electrodes spaced along the length of the distal portion of the catheter so that electrode sensors contact the coronary sinus, inferior, lateral, superior, and septal portions of the right atrium. As will be described in greater detail below, the first and second catheters may be used individually or in tandem. Although the spiral globe catheter is designed for placement in the left atrium, if during a procedure a greater distribution of spatiotemporal electrical information of the right atrium is required, the spiral globe catheter may alternatively be deployed in the right atrium.

The electrodes for both catheters include a plurality of electrically isolated electrode segments for detecting electrical signals and are arranged along each of the catheters to maximize the spatial distribution of regions sampled by the catheters. The catheters further include a plurality of electrode wires each of which are coupled to an electrode segment and extending to a proximal end portion of the electrophysiology catheter. The catheter system also includes a connector that electrically connects each of the wires to a workstation arranged to receive electrical signals detected by each electrode segment by means of the electrode wires coupled thereto. A processing unit is configured to identify each of the electrode segments and collect and process the electrophysiology information and impedance information collected by the electrode segments.

The catheter system is intended to be used in conjunction of as part of a three-dimensional mapping system. The discussed processing unit may be a three-dimensional mapping system which collects electrograms to represent the electrical activity of the heart and impedance information relative to a system of patches on the patients body for localization of the electrode positions. Some of the functions of the processing unit are to (1) collect simultaneous electrograms on each of the electrodes of the catheter system, (2) locate each of the electrodes of the catheter system relative to cardiac anatomy, (3) perform spatio-temporal analysis of data from the sensor electrodes, and (4) display analysis results on a model of the cardiac anatomy or on a model of the electrodes. An operator may then use the results to direct ablation.

The overall goal is to acquire simultaneous electrode sensor data from the greatest number of spatially dispersed locations in the left atrium, right atrium, and coronary sinus so that spatio-temporal analysis of electrode sensor data may be performed to identify mechanisms perpetuating atrial fibrillation. The pragmatic aspects are (1) the more complex the catheter design the more expensive the catheters are to produce, (2) not all areas of the atrium may be simultaneously in contact with electrode sensors, (3) introduction of catheters to the heart may involve some risks, (4) motion of the heart impact stability of the catheters, and (5) some areas of the atrium are known to be more likely perpetuating atrial fibrillation and therefore should have a higher electrode density. The exemplary embodiments are designed to substantially achieve the overall goal of panoramic atrial and coronary sinus mapping within reasonable practical limitations. The exemplary embodiments provide a spiral globe catheter that positions electrodes in a maximally dispersed distribution of an approximate globe. The spiral globe catheter may be positioned in either the left or right atrium if a single chamber is of interest. The spiral globe catheter may be positioned in the left atrium and used with a second catheter in the coronary sinus and right atrium as a catheter system. Alternatively, two spiral globe catheters may be inserted with one in each of the right and left atria. The exemplary embodiments also include a catheter system utilizing (1) a spiral globe catheter in the left atrium and (2) a RA-CS catheter in the coronary sinus and right atrium for panoramic mapping. In cardiac electrophysiology procedures, a third catheter is typically used for ablation and may be also used as a roving recording catheter to provide additional recordings as part of the catheter system for more detailed regional analysis. The ideal configuration is that of a three catheter system utilizing a spiral globe catheter, an RA-CS catheter, and an ablation catheter.

The exemplary catheter system is designed to use femoral venous groin access of the subject to allow advancement of catheters to the heart. Catheters are then positioned in the the left atrium, right atrium and coronary sinus to maximize the number of electrodes in contact with tissue and over the greatest spatial distribution. This allows for simultaneous recording of electrograms from the left atrium, right atrium and coronary sinus so that the spatio-temporal relationships between electrical activations in all three chambers may be determined. Since atrial fibrillation is often more driven by left atrial tissue than right atrial tissue, the spiral globe catheter was designed to be deployed in the left atrium and provide a greater density and dispersion of sensor electrodes in the left atrium. Specifically, the spiral globe catheter is designed to maximize the number electrodes in contact with the left atrium with the greatest spatial distribution possible for any given number of electrodes selected. The overall system yields the greatest possible panoramic sensor electrode view of atrial electrophysiology with the minimum number of electrodes.

In the following, various embodiments of the catheter system are described. Those skilled in the art will understand that the exemplary catheter system is not required to include all the features and elements described herein.

FIG. 1 shows a diagram of the left atrium, right atrium and coronary sinus in spatial relation to the other chambers and structures of the heart including the right ventricle, left ventricle, inferior vena cava, superior vena cava and mitral valve. Deployment of the spiral globe catheter into the left atrium is intended to be performed using a long sheath. The most common access site for performing electrophysiologic studies is the right or left femoral groin region and this same region will be the most likely access site for the long sheath. The long sheath may either have a fixed curve or a deflectable distal tip to further facilitate positioning of the spiral globe catheter. The long sheath is advanced to the heart and first enters the chamber of the right atrium. Using a standard technique, a trans-septal puncture will be performed to allow passage of the distal portion of the long sheath into the left atrium. The spiral globe catheter will be straightened to allow passage of the catheter into the long sheath, it will then be advanced via the long sheath to the left atrium and deployed into the left atrium. Deployment of the spiral globe catheter into the right atrium may use the same long sheath as described above with positioning of the long sheath tip in the right atrium and advancement of the catheter into the right atrium.

Deployment of the RA-CS catheter into the right atrium and coronary sinus is intended to be performed using a short sheath or a long sheath via the right or left femoral groin region depending on operator preference. The catheter will be advanced to the right atrium. Within the right atrium, the actuator will be flexed to deflect the tip of the catheter. Under fluoroscopic guidance and with manual manipulation of the actuator, the catheter tip may be advanced into the coronary sinus additional catheter may be advanced to position the right atrial portion of the catheter to have direct opposition to the inferior, lateral, superior, and septal portions of the right atrium.

Figure 2:
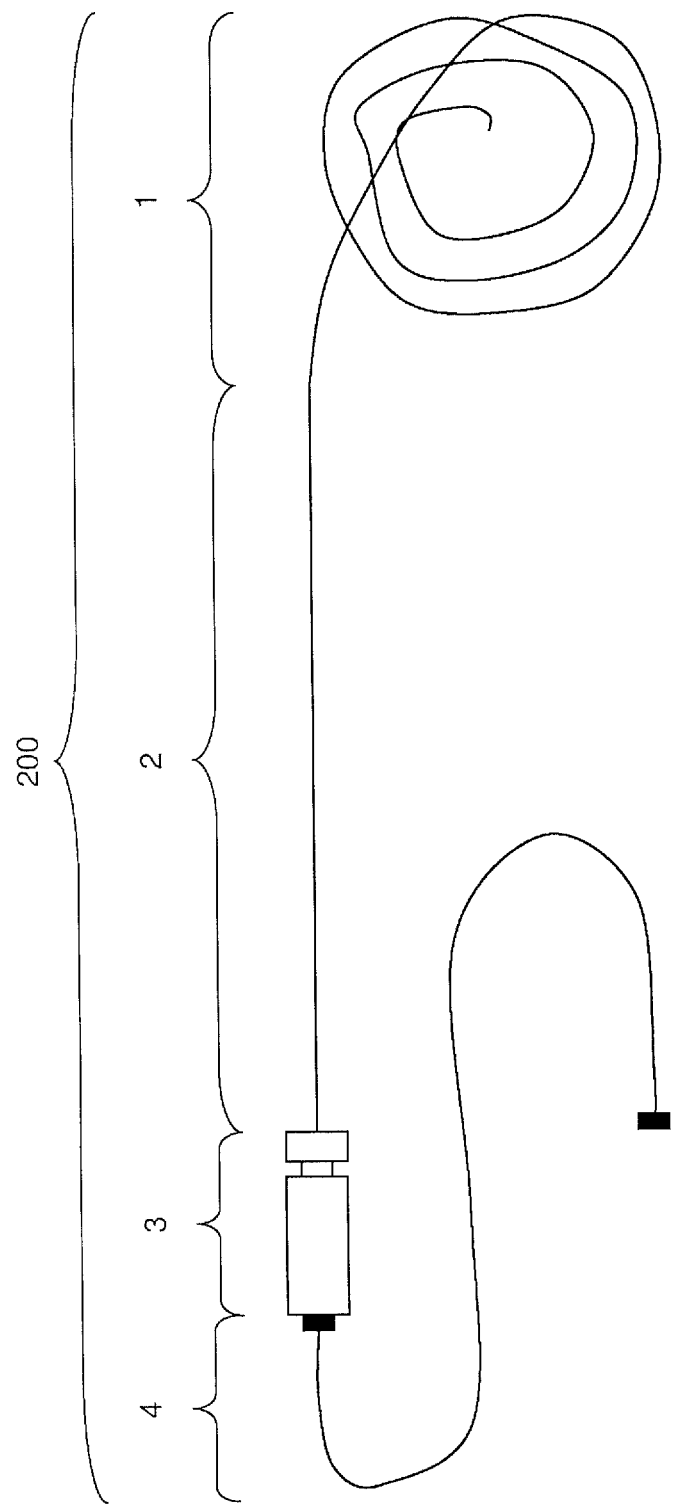
FIG. 2 shows the spiral globe catheter that comprises a spiral globe portion 1, shaft portion 2, handle portion with an actuator 3, and a connecting cable portion 4.

FIG. 2 shows the spiral globe catheter 200 that comprises the spiral globe portion 1, shaft portion 2, handle portion with an actuator 3, and a connecting cable portion 4. The sensor electrodes (not shown) are positioned on the spiral globe portion 1 as will be described in greater detail below. Those skilled in the art will understand that FIG. 2 shows the spiral globe portion 1 in an exemplary deployed position. The shaft portion 2 is used to connect the handle portion 3 to the spiral globe portion 1 and transmit the electrical signals from the sensor electrodes of the spiral globe portion 1 through the handle portion 3 and to the cable portion 4. The handle portion 3 contains an actuator that may be used to place tension on a control wire that transmits force down the shaft portion 2 to the spiral globe portion 1 to control the diameter of the spiral globe portion 1.

Figure 5:
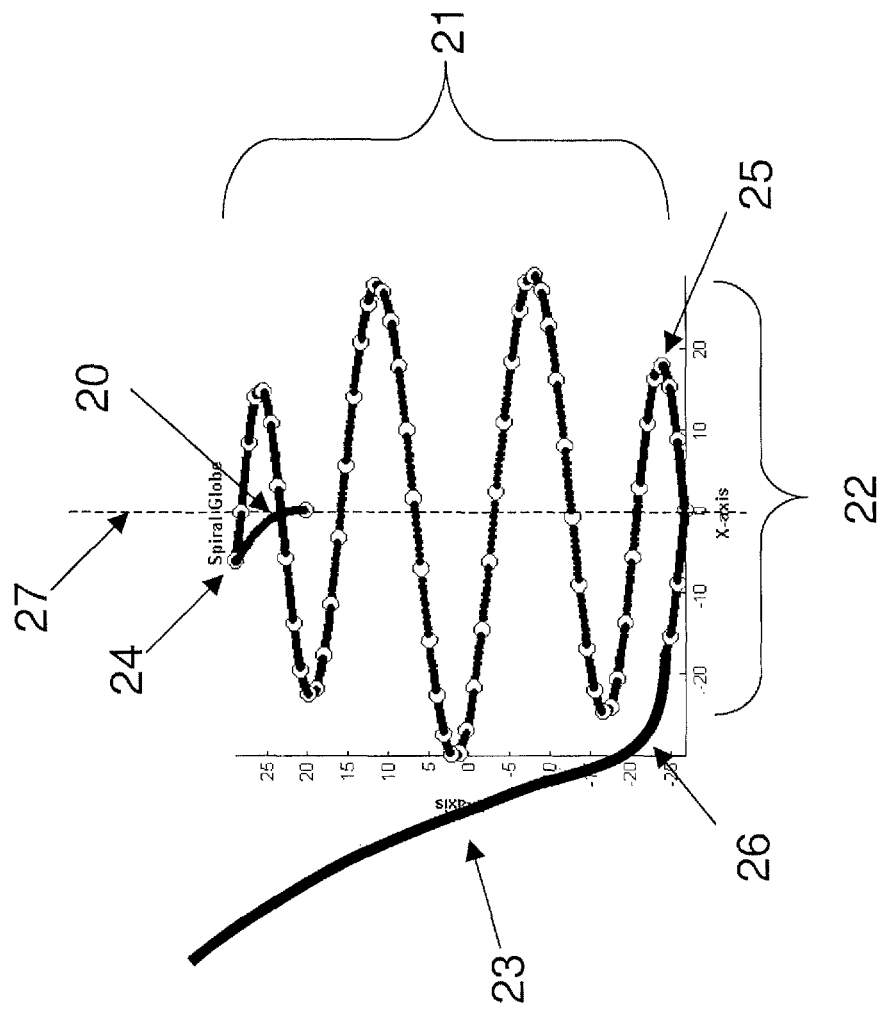
FIG. 5 shows a cranial view of the spiral globe portion of the spiral globe catheter having a distal tip 20, a body of the spiral globe 21, a mitral valve region 22, and a proximal positioning portion 23. The distal tip portion 20 joins the body of the spiral globe 21 at the location 24, which is where the catheter bends centrally away from the surface of the globe toward the center of the globe. The body portion of the spiral globe 21 joins the mitral valve portion of the spiral globe 22 at the location 25. The mitral valve portion of the spiral globe 22 joins the trans-septal portion of the spiral globe at the location 26. The spiral globe approximately rotates around a central axis 27.

FIG. 5 shows the four elements of the spiral globe portion: the distal tip 20, the spiral globe region 21, the mitral valve region 22, and the positioning region 23 (the extension from the trans-septal to the mitral valve region used for manipulating the spiral globe into position). Each of these elements will be described in greater detail below.

The distal portion ("tip") 20 of the spiral globe catheter 200 has an approximate 90 degree bend angle 24 relative to the body of the spiral globe 21. When advancing the spiral globe catheter into the left atrium via a trans-septal puncture, the preshaped 90 degree bend angle 24 is exposed and deflects the tip 20 relative to the body portion 21. Next, sequential loops of the spiral globe body 21 are advanced around the central axis 27. The tip portion 20 remains pointed towards the center of the left atrium through this process. The bend angle 24 relative to the tip 20 and next portion allows: (1) as the spiral globe portion 1 is advanced in to the atrium, the tip 200 will be projected away from atrial tissue and be protected by sequential spirals from contacting the atrium which will avoid the potential of trauma to the atrium from the tip 20; and (2) in the final position of the spiral globe portion 1, the tip 20 will not be in contact with atrial tissue which will allow placement of an electrode on tip 20 to serve as a unipolar reference for recording of electrograms from the spiral globe catheter.

The tip 20 of the spiral catheter is designed to be oriented first toward the center of the left atrium as the tip 20 is initially deployed. The tip 20 is then designed to be oriented central to the first loop of the spiral globe portion 1 so that it is protected from contact with the atrial wall. The tip 20 is designed to continue to be oriented central to the catheter as the catheter becomes fully deployed so that the tip 20 is not directed toward the atrial wall in a manner in which it could perforate the atrial wall or become entangled with the mitral valve apparatus which will be described in greater detail below.

Figure 9:
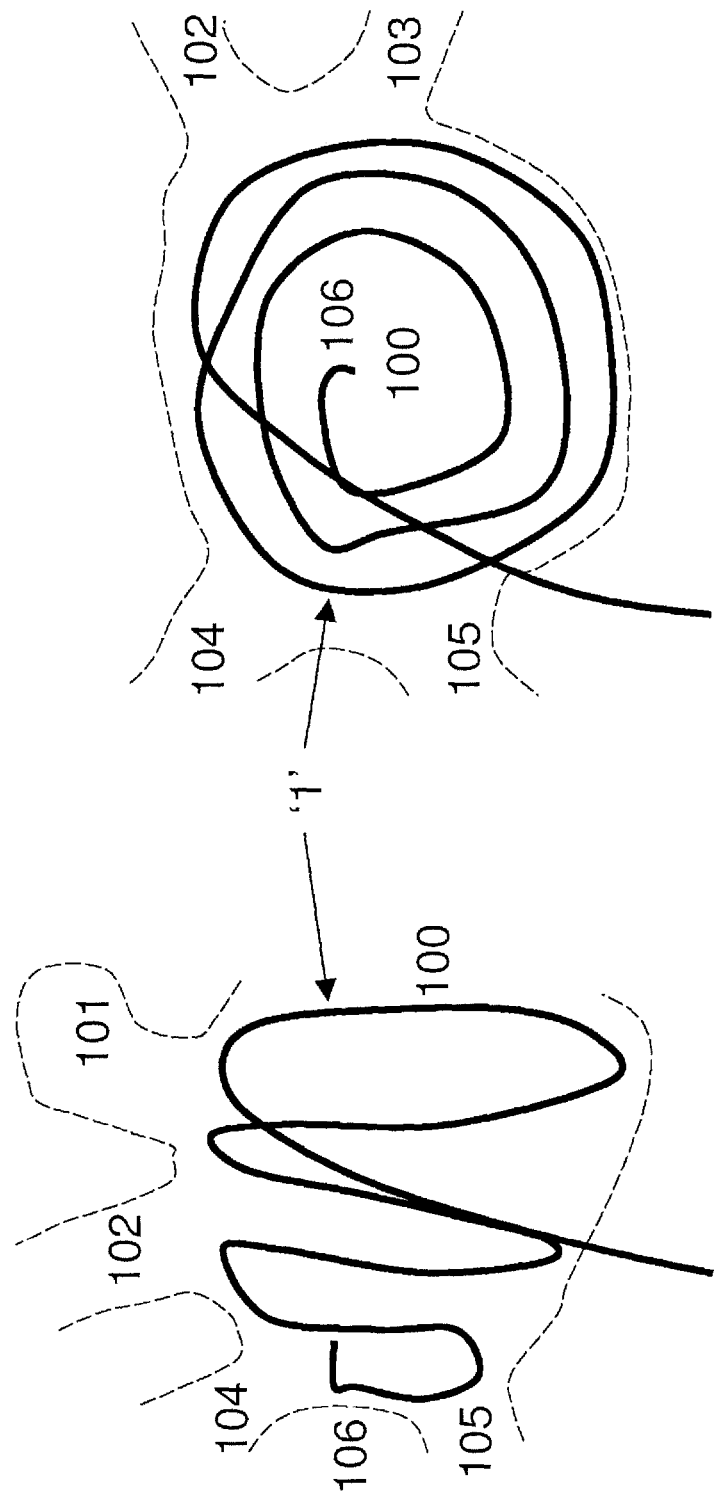
FIGS. 9A-B shows the same model of the spiral globe portion of the catheter as FIG. 5 projected the spiral globe catheter, labeled 1, relative to left atrial anatomy and associated anatomic structures. Anatomic structures associated with the left atrium are: 100 the mitral valve, 101 left atrial appendage, 102 the left superior pulmonary vein, 103 the left inferior pulmonary vein, 104 the right superior pulmonary vein, and 105 the right inferior pulmonary vein.
Figure 10:
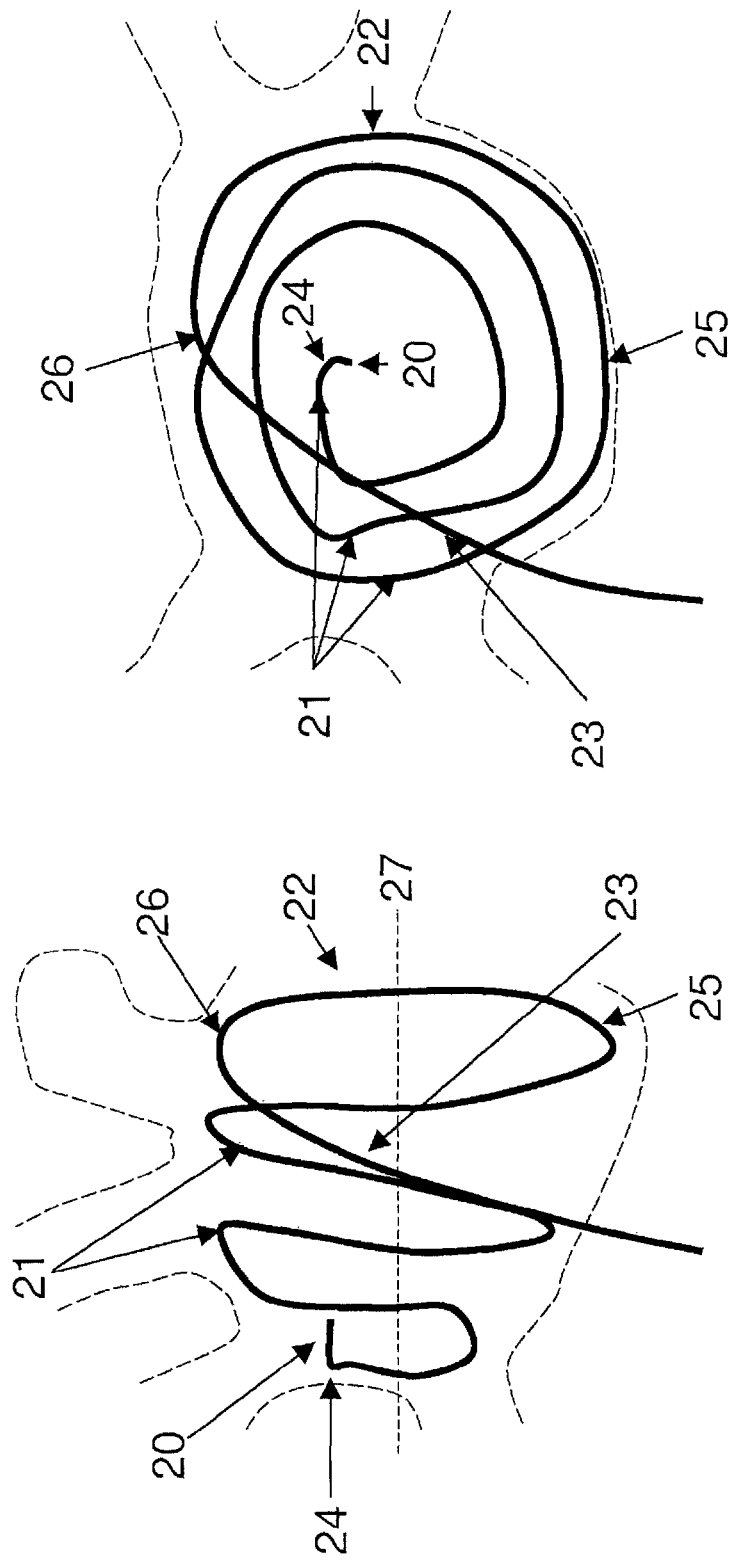
FIGS. 10A-B shows the same model of the spiral globe portion of the catheter as FIG. 9 with the same labeling of each of the portions of the spiral globe as FIG. 5. In this figure, the distal tip portion 20 is pointed away from the posterior wall of the left atrium toward the anatomic center of the left atrium. The body portion of the spiral globe 21 fills the body of the left atrium and is designed to be in contact with as many separate portions of the left atrium as possible. The mitral valve portion of the spiral globe 22 is associated with perimeter of the mitral valve anatomically. The trans-septal portion 23 transverses the anatomic interatrial septum in the typical location for performing a trans-septal puncture. The trans-septal portion 23 of the spiral globe catheter has an angle at location 26 which represents the transition to the mitral valve portion 22 of the spiral globe catheter so that the central axis labeled 27 of the spiral globe becomes oriented toward the mitral valve with the spiral advancing away from the mitral valve.

FIG. 9 shows the spiral globe catheter 1 in a fully deployed position relative to left atrial anatomy. FIG. 10 also shows the spiral globe catheter 1 in a fully deployed position relative to left atrial anatomy with regions of the spiral globe catheter labeled. FIG. 5 and FIG. 6 show the spiral globe catheter in multiple views so that the three-dimensional shape may be understood. The body portion 21 of the spiral globe catheter has sequential loops which rotate around a central axis of the globe 27.

A design parameter is the rate of precession of latitudes of the spiral globe relative to longitudes. A loop of the spiral globe may be defined as the portion of the catheter that completes a 360-degree rotation around the central axis 27 of the spiral globe as shown in FIG. 5. Using a steady precession rate of longitudes relative to latitudes, each of the loops of the spiral globe is approximately equidistant in the body portion of the spiral globe. Each of the sequential loops 21 includes a series of electrodes.

The shape of the spiral globe catheter may be maintained by a preshaped metal alloy (e.g. nickel-titanium allow) strip within the shaft of the spiral globe portion of the catheter. FIG. 14A depicts the spiral globe portion of the spiral globe catheter in cross-section with a metal strip is labeled 303 crossing the center of the catheter. The region labeled 300 is toward the center of the spiral globe catheter and the region labeled 301 is toward the outside of the spiral globe catheter. A wire labeled 302 is connected to an actuator which places tension on the wire and is designed to modify the overall diameter of the spiral globe. Additional wires labeled 304 connect the electrode elements to the connecting cable portion 8 (FIG. 3). Alternatively, the shape of the spiral globe catheter may be maintained by a metal alloy filament preshaped as a spiral globe. FIG. 14B depicts a cross-section of the spiral globe catheter with element 313 being a cross-section of a preshaped alloy filament. The region labeled 310 is toward the center of the spiral globe catheter and the region labeled 311 is toward the outside of the spiral globe catheter. A wire labeled 312 is connected to an actuator which places tension on the wire and is designed to modify the overall diameter of the spiral globe. Additional wires labeled 314 connect the electrode elements to the connecting cable portion 8 (FIG. 3).

The spiral region 21 may be defined and optimized based on the design parameters of (1) the spiral globe diameter, (2) the number of desired electrodes, (3) the aspect ratio between the inter-electrode spacing and the spacing between loops, and (4) the latitude of the opening toward the mitral valve. The latitude discussed in the following section uses the orientation of zero degrees to reflect the distal tip, the equator of the spiral globe at 90 degrees, and the opposite pole of the distal tip in the mitral valve regions as 180 degrees. Using these parameters, the design of the spiral globe may be determined as an optimization problem which iteratively converges on a solution. For a given set of parameters listed above (1-4), a single solution may be derived to optimally position electrodes along the spiral globe. The solution will include (1) the rate of precession of latitudes of the spiral globe relative to longitudes, (2) the inter-electrode spacing, and (3) the spacing between loops.

It is anticipated that the design of the spiral globe catheter may be modified according to the above constraints based on results of analysis of electrograms obtained from the catheter. Presently, the correct surface density of electrodes required to analyze atrial fibrillation is unknown. As analysis methods improve, it may be possible to reduce the required surface density of electrodes and yet still adequately characterize atrial fibrillation. FIGS. 15A-D show exemplary parameter sets which converged on solutions and the respective geometries. FIG. 15A shows a spiral globe with a 50 mm diameter, 32 electrodes, aspect ratio of 1:1, and mitral valve opening at 150 degrees. An optimized electrode location resulted in FIG. 15A with an inter-electrode distance of 14.6 mm and an inter-loop distance of 15.5 mm. FIG. 15B shows a spiral globe with a 60 mm diameter, 48 electrodes, aspect ratio of 1.5:1, and mitral valve opening at 140 degrees. An optimized electrode location resulted in FIG.

15B with an inter-electrode distance of 11.5 mm and an inter-loop distance of 18.6 mm. FIG. 15C shows a spiral globe with a 60 mm diameter, 64 electrodes, aspect ratio of 2:1, and mitral valve opening at 160 degrees. An optimized electrode location resulted in FIG. 15C with an inter-electrode distance of 8.7 mm and an inter-loop distance of 19.4 mm. FIG. 15D shows a spiral globe with a 70 mm diameter, 64 electrodes, aspect ratio of 1:2, and mitral valve opening at 140 degrees. An optimized electrode location resulted in FIG. 15D with an inter-electrode distance of 14.3 mm and an inter-loop distance of 15.3 mm.

The mitral valve region 22 of FIG. 5 is the region of the catheter oriented toward the mitral valve. The functional goals of the mitral valve region 22 is to obtain electrograms near the circumference of the mitral valve and to transition from a spiral globe curve to a circular curve with a similar latitude. With electrodes positioned around the mitral valve, electrical activation wavefronts around the mitral valve reentry may be identified. The mitral valve region 22 also provides a logical location for a hole in the overall spiral globe since the mitral valve is electrically silent and does not need to be represented by electrodes. The spacing between electrodes along the length of the catheter shaft in the mitral valve region 22 is intended to be equivalent to the spacing of electrodes along the spiral globe portion 21. The inter-loop spacing between the mitral valve region 22 and the spiral globe portion will be reduced since the mitral valve region 22 follows a near equivalent latitude. The mitral valve region 22 will include stabilizer elements similar to the spiral globe catheter portion labeled as 303 in FIG. 14A and 313 in FIG. 14B.

The positioning region 23 of FIG. 5 of the spiral globe catheter is designed to provide a preshaped transition between the shaft portion of the spiral globe catheter 2, cross the inter-atrial septum, and reach forward toward the mitral valve to the transition point 26 where the catheter then becomes oriented around the mitral valve for the mitral valve region 22. The positioning region 23 will include stabilizer elements similar to the spiral globe catheter portion labeled as 303 in FIG. 14A and 313 in FIG. 14B.

The spiral globe catheter is intended to be introduced into the left atrium through a trans-septal puncture in the interatrial septum. FIG. 13A depicts the first portion of the spiral globe catheter being introduced into the left atrium with the distal tip portion being extended into the cavity of the left atrium. FIG. 13B and FIG. 13C depict sequential loops of the body portion of the spiral globe catheter being introduced into the left atrium. FIG. 13D depicts that as the final loop of the spiral globe catheter is introduced into the left atrium which is the mitral valve portion, the proximal positioning portion is extending trans-septal toward the mitral valve and that the sheath labeled 350 is expected to rotate from being oriented toward the center of the atrium toward the mitral valve with the shape of the catheter. The metal alloy element labeled as 303 in FIG. 14A or 313 in FIG. 14B which hold the catheter shape extend from the tip of the spiral globe catheter through the proximal trans-septal portion to create and maintain the transitions and bends of the catheter labeled 25 and 26 of FIG. 5 as the catheter is introduced and positioned in the left atrium.

The spiral globe portion 1 may be defined in terms of globe geometry. The mitral valve opening is approximately a plane that faces anterior with a left anterior oblique angulation relative to the human body. There may additionally be a caudal tilt of the valve opening relatively to the human body. The position of electrodes is considered relative to the plane of the mitral valve opening wherein the XZ plane is the plane of the mitral valve opening with the X-axis being lateral to medial and the Z-axis cranial to caudal. The Y-axis is posterior to anterior relative to the mitral valve plane. The design coordinates of electrodes for the spiral globe may be defined using these axes and the Cartesian to spherical coordinate transformation.

The design parameters for placement of sensor electrodes and number of loops may be adjusted pending the results of clinical studies to increase or decrease the number of electrodes and increase or decrease the overall number of loops. Additional design parameters are the overall diameter of the spiral globe, and portion of the catheter that is open toward the mitral valve. The body portion 21 consists of a series of loops with each loop being a 360 degree rotation around the central axis (element 27, FIG. 5) and each loop crossing the same number of latitudes such that there is a constant rate of change of latitudes versus longitudes of the spiral globe body. Spacing of the electrodes is equal along the curving shaft of the catheter. The design parameters of catheter diameter, number of electrodes, inter-electrode spacing, spacing between loops, and open area toward the mitral valve determine the final geometry. In this exemplary diagram, the design parameters of a 60 mm diameter, 64 electrodes, 2:1 ratio between inter-electrodes spacing and spacing between loops, 90% of globe latitudes were specified. The resultant triangles have a distance between electrodes along the length catheter of 7.2 mm and a mean distance between electrodes of 16.3 mm between electrodes on the curl of the spiral globe.

The design of the spiral globe portion 1 helps to minimize displacement of the spiral globe portion 1 relative to the left atrium due to cardiac motion. The heart is anchored to the lungs and pleura in the left atrial posterior portion by the pulmonary veins and pericardial reflections. The left atrial posterior wall has little motion during the cardiac cycle of systole and diastole. The mitral valve is displaced toward the left ventricular apex during the cardiac cycle as blood is ejected from the left ventricle in systole. The mitral valve is displaced away from the left ventricular apex as blood fills the left ventricle in diastole. It is desirable to have electrical recordings from atrial tissue associated with proximity to the mitral valve throughout the cardiac cycle. The positioning of the final spiral or loop of the globe is to be closely associated with the mitral valve and the positioning of the tip 20 in the posterior of the left atrium is designed to allow the loops 21 of the catheter to act in a spring like manner to accommodate cardiac motion throughout systole and diastole with minimal displacement of the electrodes on the spiral globe 1 relative to the atrial tissue being recorded. Additionally, by the spiral globe portion 1 accommodating the cardiac motion of the atrium, the forces applied by the catheter to the atrium are minimized to help minimize the procedural risk of cardiac perforation.

FIGS. 6A-D shows the same model of the spiral globe portion of the catheter as FIG. 5 projected in to a right superior view (FIG. 6A), cranial view (FIG. 6B), left anterior oblique view (FIG. 6C) and a right anterior oblique view (FIG. 6D).

FIG. 7A shows the same model of the spiral globe portion of the catheter as FIG. 5 with exemplary sensor electrodes 30, 31, 32, 40, 41, 42. Each sensor electrode serves as an input to the recording system. Electrodes may be placed as a ring electrode around the length of the catheter body. An alternative design is to have the electrodes placed directionally around the outer aspect of the catheter such that the electrodes are oriented toward the outside of the spiral globe. Exemplary sensor electrodes (30, 31, 32, 40, 41, 42) are depicted in FIG. 7A as a subset of the overall number of sensor electrodes. The spatial location of each sensor electrode may be determined by the three-dimensional mapping system. The three-dimensional mapping system may then use the location of the sensor electrodes to generate a triangular mesh over the entire spiral globe with an opening toward the mitral valve.

FIG. 7B shows the exemplary sensor electrodes forming an exemplary triangular mesh. For example, along the length of the catheter in two sequential loops are electrodes 30, 31, and 32 on loop 70 and sensor electrodes 40, 41 and 42 on loop 71. The loops 70 and 71 are separated by the selected inter-loop distance (72). Edges of triangles are formed along the length of each loop between sensor electrodes. As depicted in FIG. 7B, edge 50 is between electrodes 30 and 31, edge 51 is between electrodes 31 and 32, edge 52 is between electrodes 40 and 41, and edge 53 is between electrodes 41 and 42. Next using the coordinates from the three-dimensional mapping system, the edges between the loops of the catheter are determined by the minimal distance between sequential electrodes. This may be determined using a Euclidian distance measure or angular distance measure. As depicted in FIG. 7B, triangle 60 is generated from the electrode sensors 30, 40, and 31 along with edges 50, 54 and 55; triangle 61 is generated from the electrode sensors 40, 31, and 41 along with edges 52, 55 and 56; triangle 62 is generated from the electrode sensors 31, 41, and 32 along with edges 51, 56 and 57; and triangle 63 is generated from the electrode sensors 41, 33, and 42 along with edges 53, 57 and 58.

The exemplary catheter system is designed to be used as an input to a recording system and three-dimensional mapping system. The design results in an approximate even distribution of sensor electrodes over the surface of the spiral globe portion 1. The design also allows for physical properties of the catheter to adjust the electrode spacing and loops of the catheter to optimize the design. For example, it may be determined that due to the physical properties of the catheter or due to other procedural concerns, fewer loops of the catheter are desired. The inter-electrode spacing relative to inter-spline spacing design parameters may be adjusted to accommodate this change.

FIGS. 7-8 show the same model of the spiral globe portions of the catheter as FIGS. 5-6 with the resultant triangular mesh depicted in multiple orthogonal views. As described above, the triangular mesh may be calculated using the sensor electrode coordinates of the three-dimensional mapping system across the entire spiral globe. A complete triangular mesh is depicted in FIG. 8 with a right superior view (FIG. 8A), left anterior oblique view (FIG. 8B), right posterior oblique view (FIG. 8C), right anterior oblique view (FIG. 8D), superior or cranial view (FIG. 8E), and a left posterior oblique view (FIG. 8F). The triangular mesh may also be used as a design parameter. For example, a majority of the triangles are of similar size. Triangles which are of a dissimilar size occur at the distal pole (FIG. 8C). It may be desired to move the sensor electrode, move the distal tip angle position, or place additional sensor electrodes near the distal pole to minimize distortion of triangles so that all edges between electrodes are of similar length. This may be programmed as a design parameter and optimized.

An actuator in the handle 3 of the catheter may be used to deliver tension on a wire contained within the shaft of the catheter and extending to the distal tip. FIG. 14 illustrates two examples of an actuator wire and stabilizer configurations. FIG. 14A shows a cross-section with 300 being the inner aspect of the spiral globe catheter (toward center of left atrium), 301 being the outer aspect of the spiral globe catheter (toward contact with the left atrium). An actuator wire 302 is contained within the compartment toward 300 and a stabilizer metal alloy strip 303 which maintains the shape of the spiral globe. The stabilizer metal alloy strip 303 acts as a compression element when a tension is applied to 302 to result in a controlled shape change in the geometry of the spiral globe such that each loop of the spiral globe is similarly reduced in diameter to control the overall diameter of the spiral globe. Also included in the cross-section are electrical wires 304 for connecting the sensor elements to the proximal handle FIG. 2 element 3. FIG. 14B shows an alternative configuration cross-section with 310 being the inner aspect of the spiral globe catheter (toward center of left atrium), 311 being the outer aspect of the spiral globe catheter (toward contact with the left atrium). An actuator wire 312 is contained within a channel compartment toward 310 and a stabilizer metal alloy filament (e.g., nickel-titanium alloy) 313 which maintains the shape of the spiral globe. The stabilizer metallic filament 313 acts as a compression element when a tension is applied to 312 to result in a controlled shape change in the geometry of the spiral globe such that each loop of the spiral globe is similarly reduced in diameter to control the overall diameter of the spiral globe. There are two channels 314 which contain the electrical wires for connecting the sensor elements to the proximal handle FIG. 2 element 3.

Figure 11:
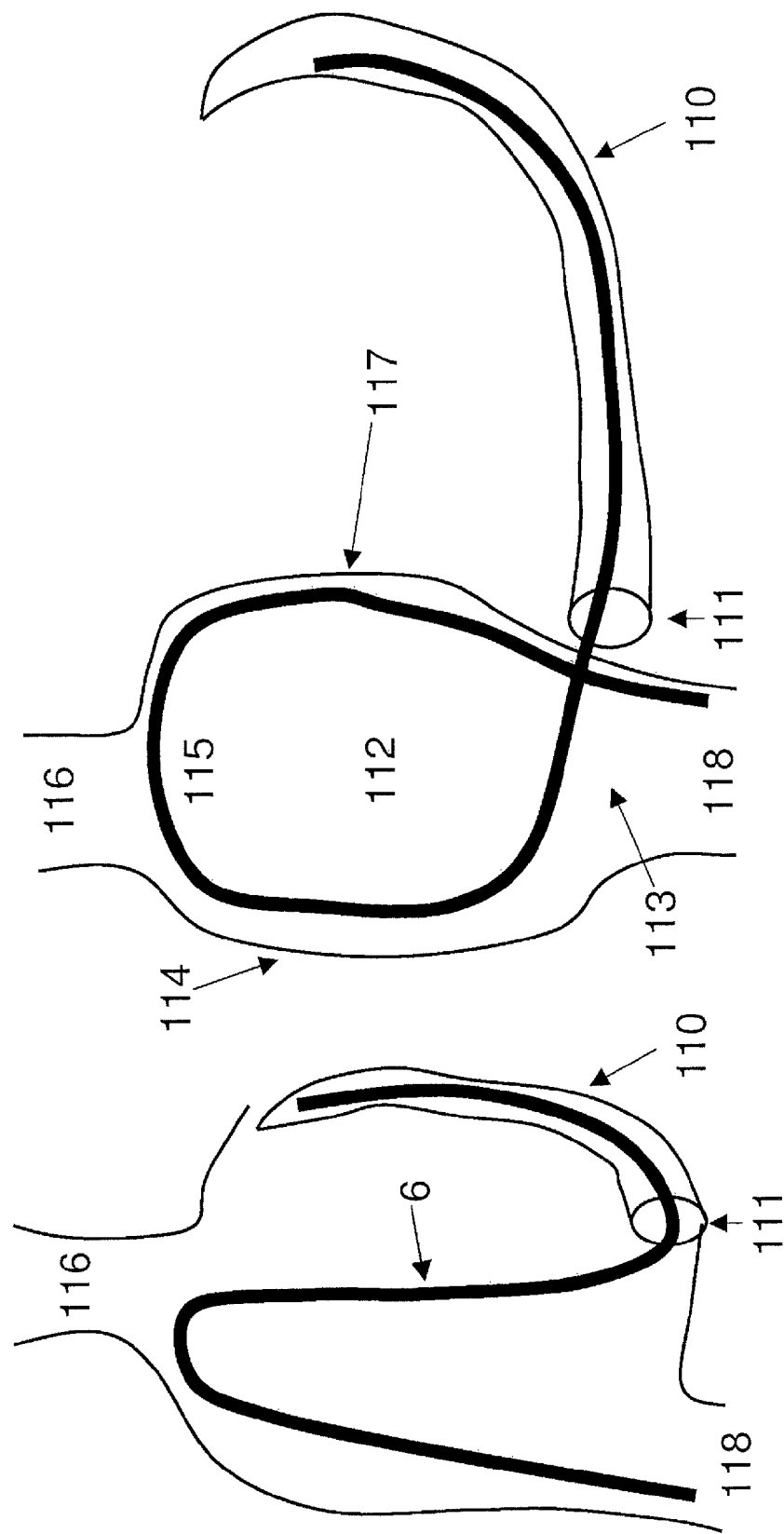
FIG. 11A shows a right anterior oblique view and FIG. 11B shows a left anterior oblique view show the right atrial-coronary sinus (RA-CS) catheter in position relative to the coronary sinus 110, ostium of the coronary sinus 111, body of the right atrium 112, cavo-tricuspid isthmus 113, lateral right atrium 114, superior right atrium 115, superior vena cava 116, septal right atrium 117, and inferior vena cava 118.
Figure 12:
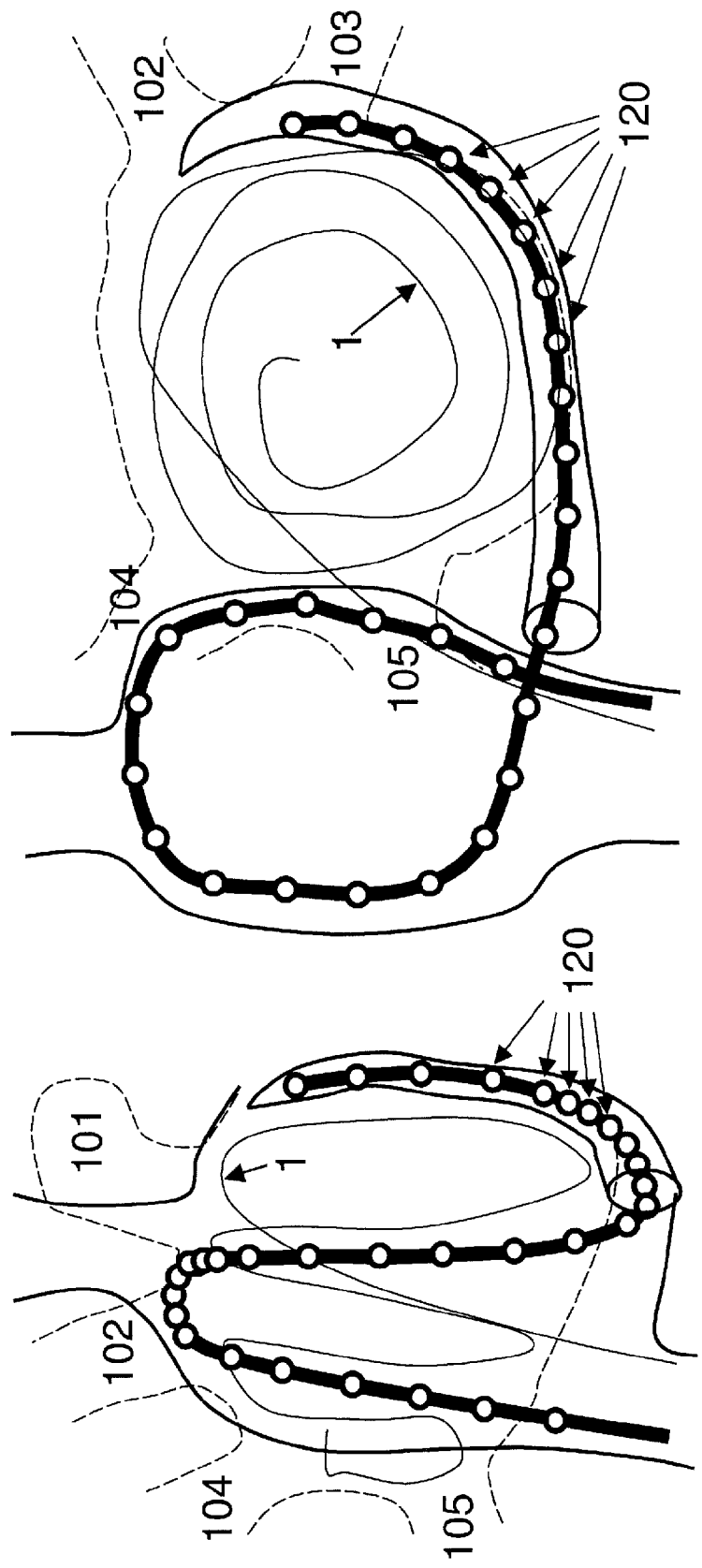
FIG. 12A and FIG. 12B correspond to FIGS. 11A and 11B respectively. Additionally, the spiral globe catheter 1 is shown in position in the left atrium. The left atrial appendage 101 and pulmonary veins 102, 103, 104, and 105 are labeled the same as in FIG. 9. Electrode sensors 120 are aligned along the shaft of the RA-CS catheter and are in proximity to the coronary sinus, ostium of the coronary sinus, cavo-tricuspid isthmus, lateral right atrium, superior right atrium, and septal right atrium.

FIG. 3A shows the right atrial-coronary sinus catheter (RA-CS catheter) 201 in a straight position comprising a distal recording portion 5, shaft portion 6, handle portion with an actuator 7, and a connecting cable portion 8. FIG. 3B shows the RA-CS catheter curved to reflect the deployed position in the right atrium and coronary sinus similar to the catheter and anatomy depicted in FIG. 11. FIGS. 12A and 12B illustrate the sensor electrodes 120 are positioned on the distal recording portion which corresponds to FIG. 3 portion 5. The shaft portion 6 is used to connect the handle portion 7 to the distal recording portion 5 and transmit the electrical signals from the sensor electrodes of the distal recording portion 5 through the handle portion 7 and to the cable portion 8. The handle 7 contains an actuator that may be used to place tension on a control wire that transmits force down the shaft to the RA-CS catheter to control the arc of the distal RA-CS catheter.

A concern for catheter designs that are deployed in the left atrium is the risk of thrombus formation which could dislodge and cause an ischemic stroke or other systemic embolism. Areas of catheter designs which include the juncture of multiple elements may result in relative stasis of blood and an increase in risk of thrombus formation. The exemplary embodiments are designed to be a single element with no such junctures which could increase the risk of thrombus formation. This may allow the catheter design of the exemplary embodiments to be safer than other catheters designed to be deployed in the left atrium.

Atrial fibrillation is a complex arrhythmia that involves the left atrium, right atrium, and coronary sinus. Optimal analysis of atrial fibrillation would include analysis of all three of these chambers simultaneously. Thus, an additional catheter to the spiral globe catheter is desired for complete mapping of atrial fibrillation. The spiral globe catheter and the RA-CS catheter are designed as a pair of catheters that position a plurality of electrode sensors in dispersed locations of the atrium so that those catheters may record a plurality of simultaneous electrograms for analysis. Each catheter may be used independently for electrogram analysis. However, the preferred embodiment of this design is use of both catheters.

Figure 4:
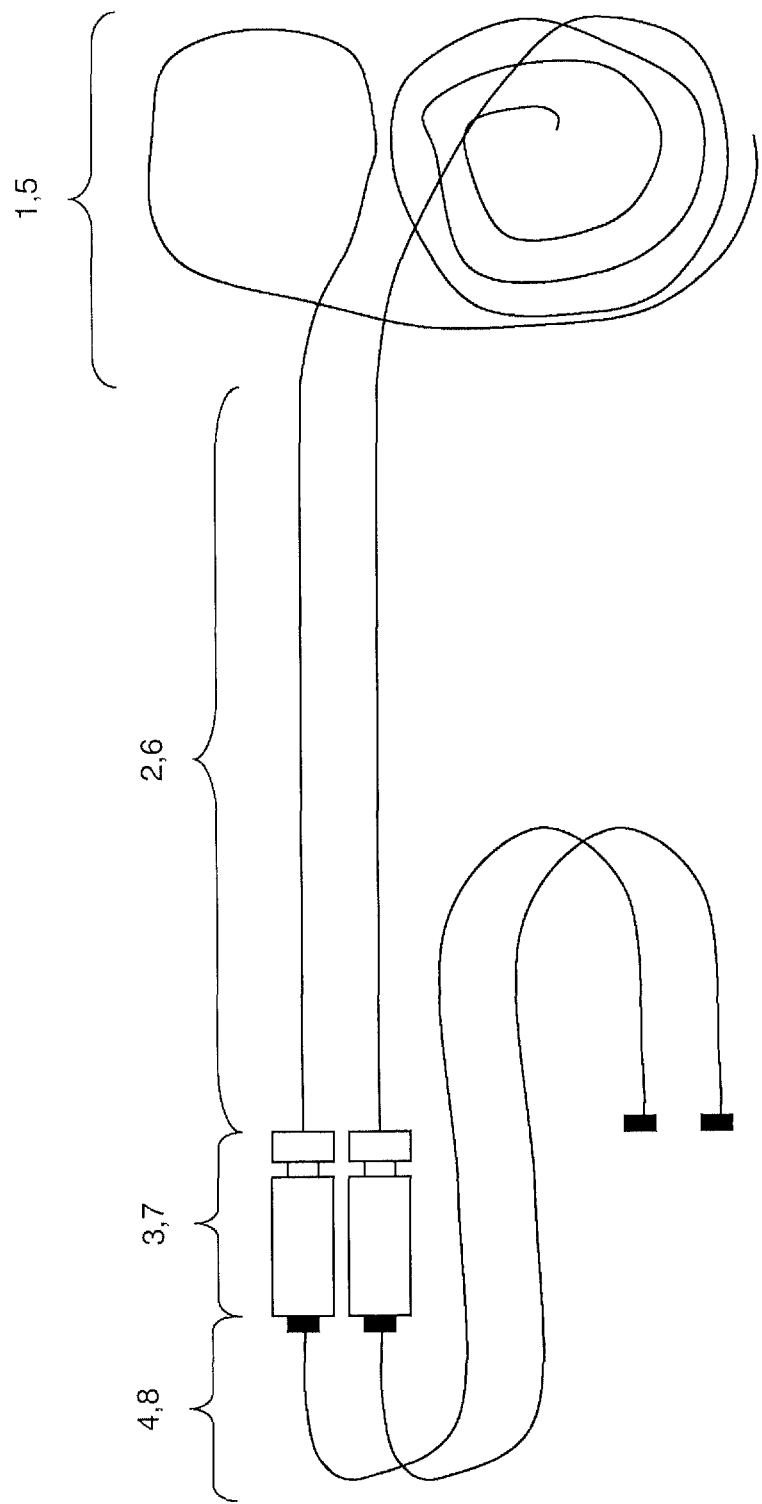
FIG. 4 shows the catheter system with the spiral globe catheter and RA-CS catheter in relative position once deployed in the left atrium, right atrium and coronary sinus.

FIG. 4 shows the catheter system with the spiral globe catheter and RA-CS catheter in relative position once deployed in the atrium. As shown in FIG. 4., the spiral globe catheter and the RA-CS catheter share similar design components of the shaft portion (2, 6), handle portion (3, 7), and connecting cables (4, 8). The differences in the catheter lie in the design of the distal portions 1 and 5. Each catheter he has a plurality of electrode sensors in the distal portion which are use for recording electrical potentials. The heart is an electrically active organ which produces wavefronts of electrical activity from cycles of cell membrane depolarization and repolarization which result in an extracellular electrical potentials. These extracellular electrical potentials may be measured by the electrode sensors of the catheters and when combined with a mapping system may generate a map of the hearts electrical activity.

Additional sensors to the electrodes sensors may be placed on the spiral globe catheter and the RA-CS catheter. In the preferred design, the catheters are to be used with a three-dimensional mapping system. An example of additional sensors are magnetic sensors may be placed on the catheters to sense the magnetic fields used with a three-dimensional mapping system. Thus, the catheter positions may be measured relative to the three-dimensional mapping system using the additional sensors.

Figure 17:
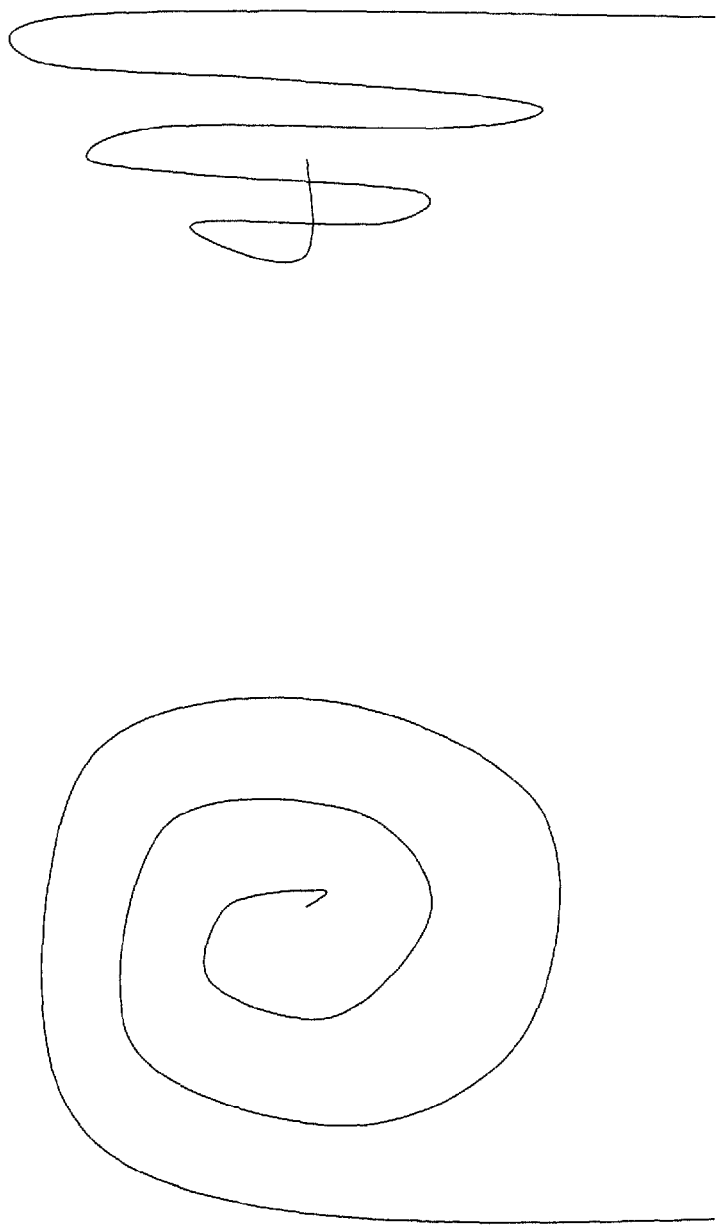
FIGS. 17A-B shows an exemplary conical helix catheter. The body portion of the catheter may also be described as being a spiral around a cone with a geometric progression of distance between sequential loops.
Figure 18:
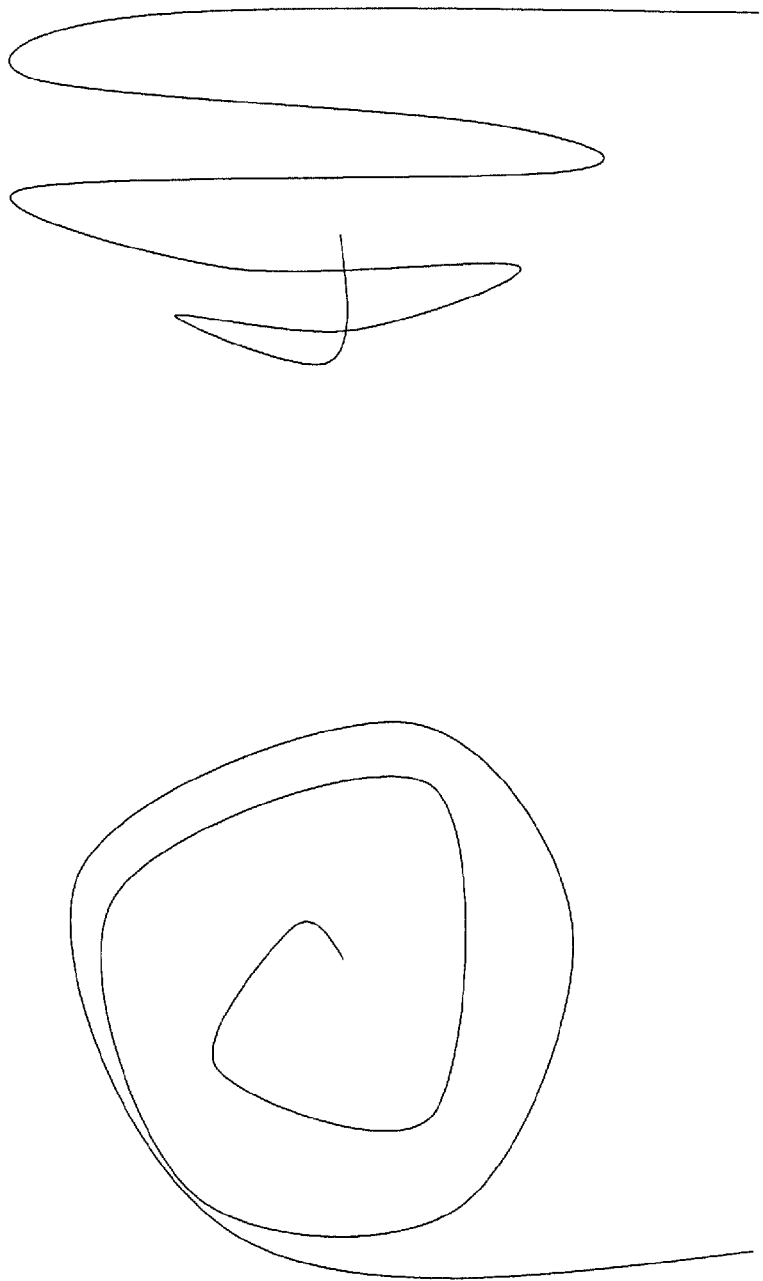
FIGS. 18A-B shows exemplary hemisphere spiral catheter. This catheter is half of a spiral globe starting at the equator of the globe.
Figure 19:
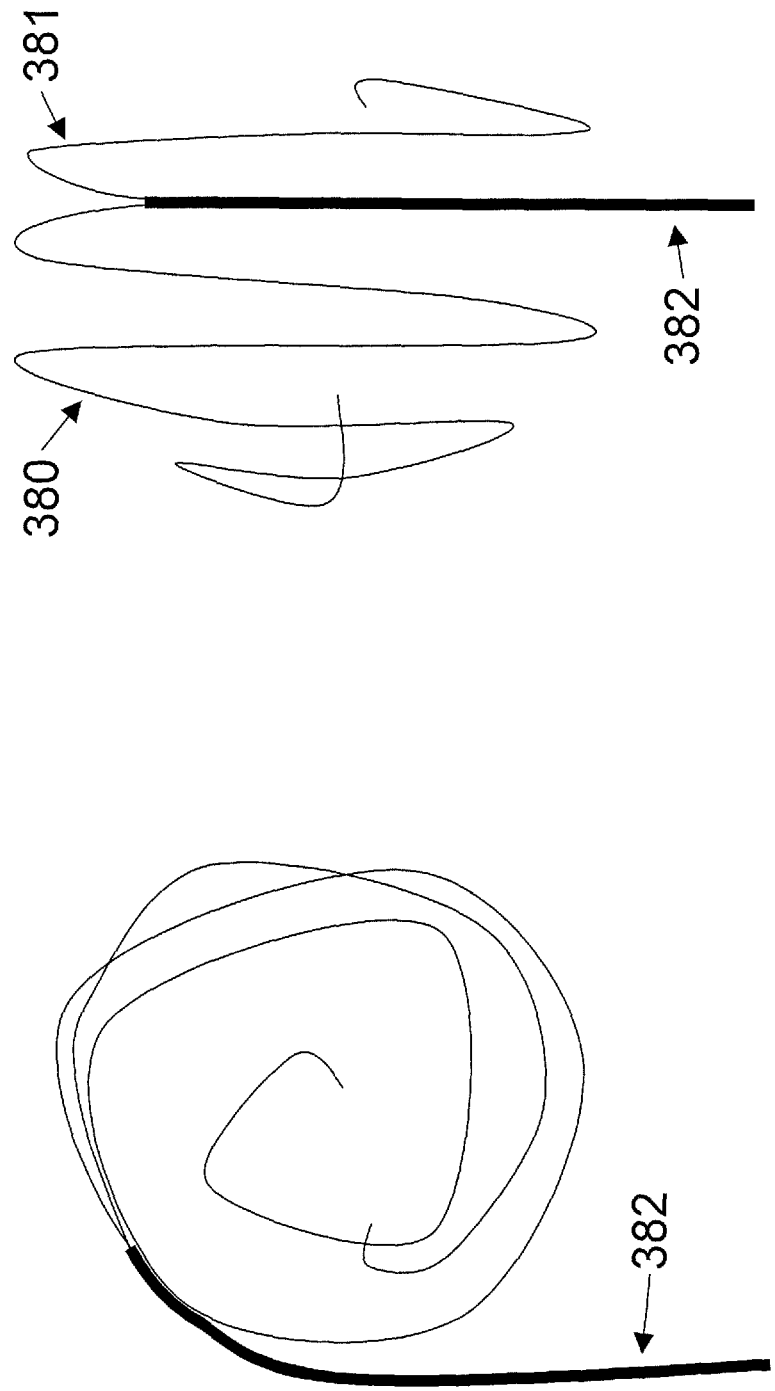
FIGS. 19A-B shows exemplary duo-spiral globe catheter with independent tips. This catheter has two spirals which separate approximately at the equator of the globe and spiral in opposite directions.
Figure 20:
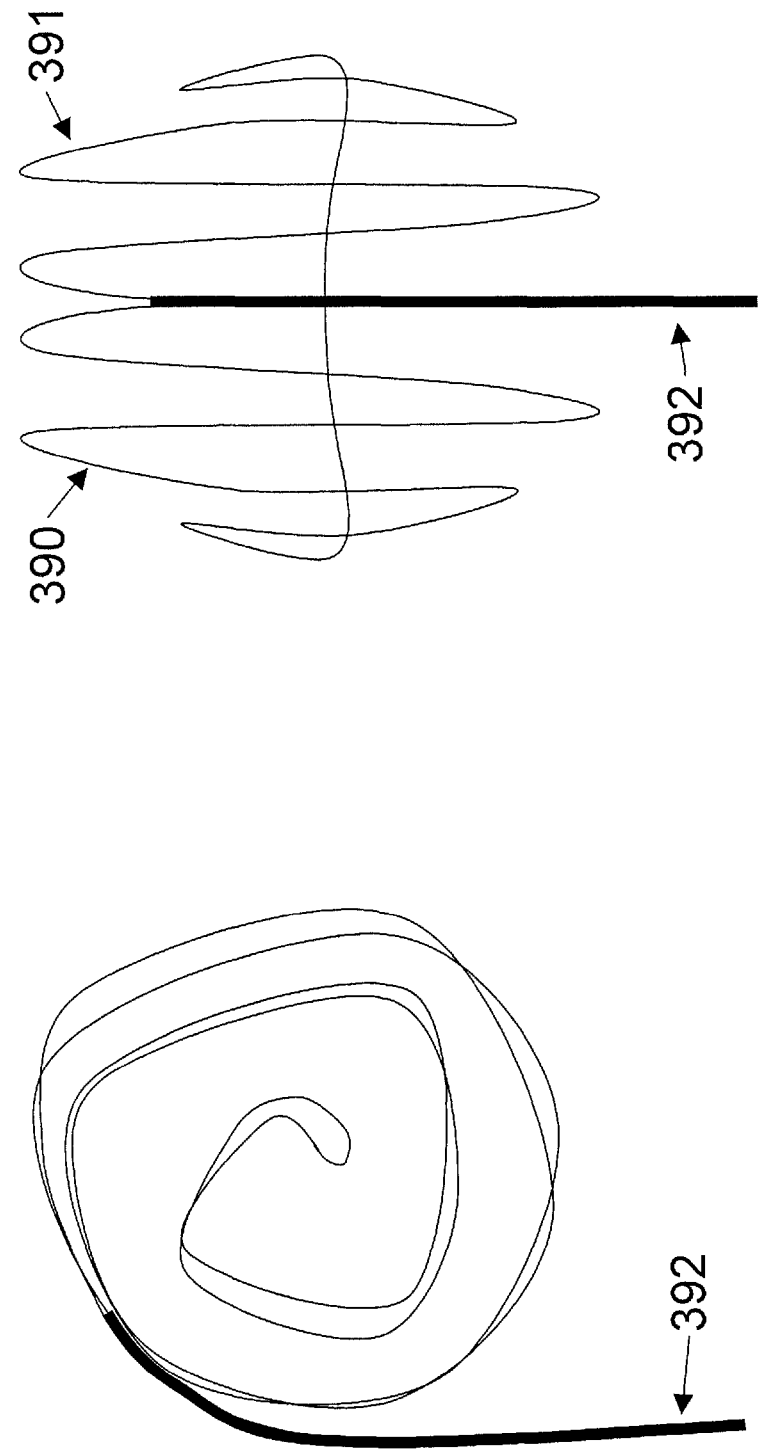
FIGS. 20A-B shows exemplary duo-spiral globe catheter with connected tips. Similar to FIG. 19A-B, this catheter has two spirals which occupy opposite hemispheres. An additional modification is to have the tips connected to further stabilize the catheter.

The spiral globe catheter fulfills the specified design goal of maximally dispersing electrode sensors to contact as many areas of the left atrium as possible within reasonable manufacturing constraints. The spiral globe describes the body portion of the catheter. Additionally, the spiral globe is modified by having a tip portion, a mitral valve portion, and a trans-septal portion. Additional shaped catheters related to the spiral globe catheter may fulfill or partially fulfill the specified design criteria which includes electrodes spaced on a series of spirals with approximately equal distance between spirals and may or may not have additional modification to a tip portion, mitral valve portion, and/or a trans-septal portion. The additional shaped catheters are described as a helix catheter (FIG. 16), a conical helix catheter (FIG. 17), a hemisphere spiral catheter (FIG. 18), a duo-spiral globe catheter with independent tips (FIG. 19), and a duo-spiral globe catheter with connected tips (FIG. 20).

The helix catheter or spiral cylinder catheter (FIG. 16) has a body portion of the catheter consisting of a series of spiral loops that are approximately equidistant apart around a substantially cylindrical shape. The catheter may have the tip portion modified to allow the tip to be directed toward the center of the catheter or anatomic chamber similar to the design of the spiral globe catheter. The exemplary catheter shown in FIG. 16 does not have additional modifications to direct the body of the helix toward the mitral valve, but may be modified to include a mitral valve portion and a trans-septal portion similar to the spiral globe catheter.

The conical helix catheter or spiral cone catheter (FIG. 17) has a body portion of the catheter consisting of a series of spiral loops that are approximately equidistant apart around a substantially conical shape. The catheter may have a tip portion modified to direct the distal tip of the catheter toward the center of the catheter or anatomic chamber. The catheter shown in FIG. 17 does not have additional modifications to direct the body of the helix toward the mitral valve, but may be modified to include a mitral valve portion and a trans-septal portion similar to the spiral globe catheter.

The hemisphere spiral catheter (FIG. 18) has a body portion of the catheter consisting of a series of spiral loops that are approximately equidistant apart around a substantially globe shape. The catheter may have a tip portion modified to direct the distal tip of the catheter toward the center of the catheter or anatomic chamber. The catheter shown in FIG. 17 does not have additional modifications to direct the body of the helix toward the mitral valve, but may be modified to include a mitral valve portion and a trans-septal portion similar to the spiral globe catheter.

The duo-spiral globe catheter with independent tips (FIG. 19) is a catheter which splits from being a single shaft element 382 into two separate spiral elements. The split occurs at the approximate equator of a globe and each spiral extending approximately symmetrically opposite away from the equator with a similar rate of latitude per longitude. The spiral element 380 toward the posterior of the left atrium and the spiral element 381 extends anterior toward the mitral valve. The potential advantages of the duo-spiral globe catheter with independent tips over the spiral globe catheter are: (1) the electrodes are split onto two spirals so that then number of electrode elements per spiral is reduced and may allow for smaller diameter catheter, (2) the element 381 extends toward the mitral valve such that the trans-septal portion extending toward the mitral valve of the spiral globe element 23 (FIG. 5) is not necessary, and (3) the actuator(s) controlling the diameter of the spirals follow one primary curve may be less prone to geometric distortion than the spiral globe catheter which has curve element 26 (FIG. 5) which is not in the same orientation as the curve of the spiral globe body element 21 (FIG. 5).

The duo-spiral globe catheter with connected tips (FIG. 20) is a catheter that is similar to the duo-spiral globe catheter with independent tips (FIG. 19) but has a union of the independent tips to form a continuous catheter. The catheter splits from being a single shaft element 392 into two separate spiral elements. The split occurs at the approximate equator of a globe and each spiral extending approximately symmetrically opposite away from the equator with a similar rate of latitude per longitudinal. The spiral element 390 toward the posterior of the left atrium and the spiral element 391 extends anterior toward the mitral valve. The tips which extend toward the center of the spiral globe are connected in the manufacturing process to give greater stability to the overall shape of the duo-spiral globe. The connection of the tips may result in a reduced cardiac perforation risk since there is no longer an exposed tip. The duo-spiral globe catheter with connected tips has the same advantages as the duo-spiral globe catheter with independent tips and given the greater stability imparted by connecting the tips may yield an overall more usable catheter. The duo-spiral globe catheter with connected tips is symmetric and does not have a specific mitral valve portion. This may allow the catheter to be easier to position in the left atrium or right atrium since it is not orientation dependent.

Figure 21:
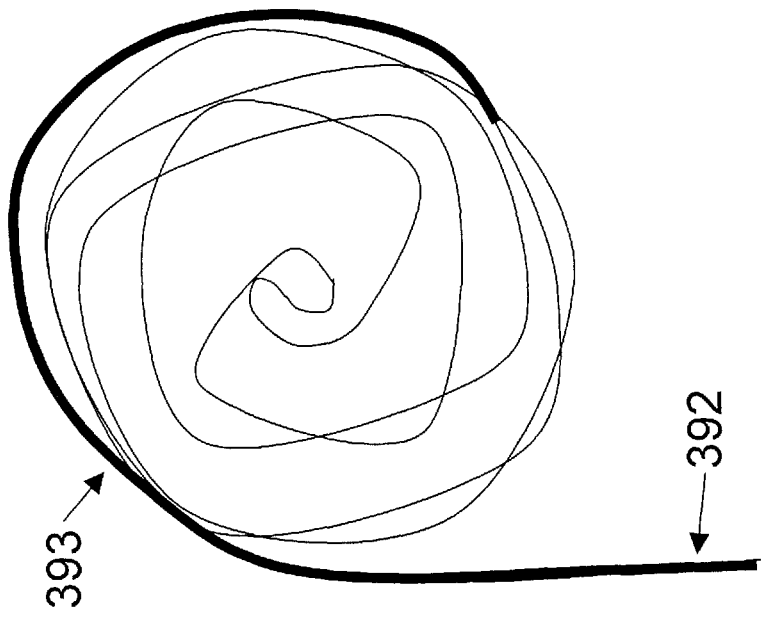
FIG. 21 depicts the same duo-spiral globe catheter with connected tips as FIG. 20.

The duo-spiral globe catheter designs (FIGS. 19 and 20) may have an actuator to control the overall diameter of the globe as discussed in the preceding sections. Additionally, the duo-spiral globe catheter designs may have electrode sensors placed on the shaft portion of the catheter. This would allow for an additional method for resizing the diameter of the globe. The shaft portion of the spiral globe could be advanced further into the atrium to form an additional electrode loop of the duo-spiral globe and a larger diameter globe. FIG. 21 depicts the same duo-spiral globe catheter with connected tips as FIG. 20. FIG. 21 shows the catheter in a position with an additional one half loop or 180 degree rotation of the duo-spiral globe with the single shaft element 392 extending into the atrium. The act of extending the catheter further into the atrium may further expand the diameter of the duo-spiral globe as needed by an operator to optimize tissue contact and therefore recording of electrical signals from the heart.

The longitudinal spiral globe catheter (FIGS. 23 and 24) is a design that is related to both a conventional globe catheter and the spiral globe catheter (FIGS. 5-10). The conventional approach to a globe shaped catheter has been to create a catheter with multiple splines wherein each spline is aligned to a longitude of the globe from the proximal to the distal, pole and each spline contains multiple electrodes. Splines are oriented along the longitudes of a globe with equal spacing between longitudes. Each of the splines has a single circular bend within a single plane. A conventional globe catheter has 64 electrodes and eight splines with each spline containing eight electrodes. In this conventional catheter, the electrodes are arranged with equal latitudes around the globe such that the electrode positions may also be transformed into a rectangular grid configuration of equal latitudes and longitudes.

One limitation of the conventional globe catheter design is the electrode spacing is not ideal for recording atrial signals. In this conventional design, the inter-spline distance around the equator of the central axis, and hence the inter-spline inter-electrode distance, is determined by the number of splines divided by the circumference of 360 degrees. This results in large distances between electrodes around the equator of the globe. The conventional globe catheter has evenly spaced electrodes along a portion of the spline and with no electrodes near the tip or proximal portions such that there are areas with poor coverage at the tip and proximal portions. A typical conventional globe catheter has 8 splines, 8 electrodes per spline, a diameter of 50 mm, and electrodes spaced evenly at 15 degree increments from 25 to 130 degrees. This results in a maximum inter-spline inter-electrode distance at the equator of the globe of 19.25 mm and intra-spline inter-electrode distance of 6.33 mm. If rectangles are created from these electrodes, then the ratio of the edges between the splines to along the splines is 3.04 and there remain areas at the tip and proximal portions with no coverage of electrodes. Overall, the result is a very non-uniform sampling of the surface of the globe.

A second limitation of the conventional globe catheter design is that when the size of the catheter does not anatomically fit a chamber of the heart well, the splines tend to bend near the poles such that there is bunching of splines together with similar longitudes which further exacerbates the inter-spline inter-electrode distance problem discussed above. One goal of the inventive catheter is to have the catheter deform in a uniform manner when it accommodates to a chamber of the heart to preserve the inter-electrode spacing and continue to provide uniform sampling. The conventional globe catheter design performs poorly when attempting to position the catheter in the heart due to bending of the splines toward different latitudes.

Improved electrode spacing may be used to improve electrode coverage of a conventionally shaped globe catheter. Similar to the spiral globe catheter, electrodes may be used to form vertices of a triangular mesh. Electrodes may be placed along a greater portion of the spline and staggered on even and odd numbered splines to form a relatively uniform triangular mesh. FIGS. 22A-D show a new globe catheter with a new electrode spacing pattern to create more uniform sampling of electrodes across the globe surface. Using a nomenclature of the tip pole being zero degrees and the proximal shaft pole being 180 degrees, FIGS. 22A-D show a globe catheter with improved electrode spacing with electrodes on odd splines (e.g., splines labeled A, C, E, G) placed from 10 to 160 degrees at 20 degree intervals and electrodes on even splines (e.g., splines labeled B, D, F, H) placed from 20 to 170 degrees at 20 degree intervals. In this model, the result has a maximum inter-spline inter-electrode distance at the equator of the globe of 19.63 mm and intra-spline inter-electrode distance of 7.9 mm. If triangles are created from these electrodes, then the maximum ratio of the triangular edges between the splines to along the splines is 2.48. There is improved coverage at both the tip and proximal portions of the globe resulting in improved sampling of the surface of the globe.

The longitudinal spiral globe catheter shown in FIGS. 23A-D is a new catheter design that is a substantial modification of the conventional globe catheter. The longitudinal spiral globe catheter may be thought as related to the spiral globe catheter in that an element or elements with electrodes form a spiral along the surface of a globe and rotate around a central axis. The spiral globe catheter has additional modifications to accommodate to the left atrium and has one element rotating around the central axis. The longitudinal spiral globe catheter has multiple elements that rotate around the central axis. These multiple elements, or splines, contain sensors for electrical signals and positional information. The longitudinal spiral globe catheter is designed to have electrodes positioned to maximize the distance between sensors to result in sampling the greatest distribution of cardiac tissue.

The shape of the longitudinal spiral globe catheter may be maintained by splines based on a preshaped metallic alloy, e.g., nickel-titanium which are joined to the catheter shaft and are stabilized at the distal tip. Importantly, the splines are each the same uniform shape.

The longitudinal spiral globe catheter may be built with any number of splines which fulfill the criteria of being a spiral around the central axis of the globe. In practical terms, it is expected that the maximum number of splines would be eight. Use of even and odd splines allow for improved electrode spacing as discussed in the above section regarding FIGS. 23A-D globe catheter with improved electrode spacing. The number of splines may be 2, 4, 6 or 8. The number of splines impacts the structural rigidity of the catheter and the number of electrodes required to be placed along each spline. A smaller number of splines results in less structural support and may be less desirable. Using conventional electrode design, an increase in the number of electrodes per spline results in an increase in manufacturing difficulty. Overall, the preferred number of splines may be 8 or 6, but as described above, this number may be altered based on the factors discussed above.

The slope of the spiral of the longitudinal spiral globe catheter is a function of the latitude. The slope of the spiral is at zero degree at each the tip pole and proximal pole. The slope of the spiral increases to a maximum at the equator and then decreases. Parameters for the longitudinal spiral may be created with the following method. A conventional globe catheter may be described in terms of spherical coordinates with azimuth or longitude, elevation or latitude and radius. Each spline has a same valued azimuth equally spaced around the circumference of the globe. Each spline has an elevation varying from positive half pie radians at the tip pole, zero at the equator, and negative half pie radians at the proximal pole. The longitudinal spiral globe has a rotational magnitude applied to each of the splines of the conventional spiral globe design. A magnitude of the rotation of the spline in radians may be used as a parameter in modeling the longitudinal spiral globe. The magnitude of the rotation of the spine multiplied by the elevation may be added to the azimuth to create and new value for the azimuth, and hence a spiral with the magnitude of the spiral zero at each of the poles and a maximum at the equator. Another manner of describing the above rotated splines is that each spline curves about a longitudinal axis of the globe as a function of the latitude of the globe.

FIG. 23 A-D shows a longitudinal spiral globe catheter with eight splines and a magnitude of the rotation of the spine being one-fourth pie radians. FIG. 24 A-D shows a longitudinal spiral globe catheter with six splines and a magnitude of the rotation of the spline being one-third pie radians. FIGS. 23A-D and 24A-D show symmetrically rotated splines where a slope of the curves is a minimum at the poles (in this example the slope is 0 at the poles) and a maximum at the equator. However, it is also possible to have asymmetrically rotated splines where the maximum slope of the curves is at a location other than the equator.

The odd and even labeled splines have offset electrode positions to create a more uniform electrode distribution. The locations of each electrode may be described by a position along the length of each spline. For example, if the length of a spline is 9.5 cm and the design calls for 8 electrodes, then electrodes on odd labeled splines may be placed at 1.0, 2.0, 3.0, 4.0, 5.0, 6.0, 7.0, and 8.0 cm and electrodes on even labeled splines may be placed at 1.5, 2.5, 3.5, 4.5, 5.5, 6.5, 7.5, and 8.5 cm. Between electrodes on even and odd splines there is a 50% staggering of electrode positions. At the tip and proximal poles, there is either a 1.0 or 1.5 cm from the pole. This electrode configuration may be proportionally applied to any spline length. Using theses proportions, the electrodes were placed in FIGS. 22, 23, and 24.

Figure 26:
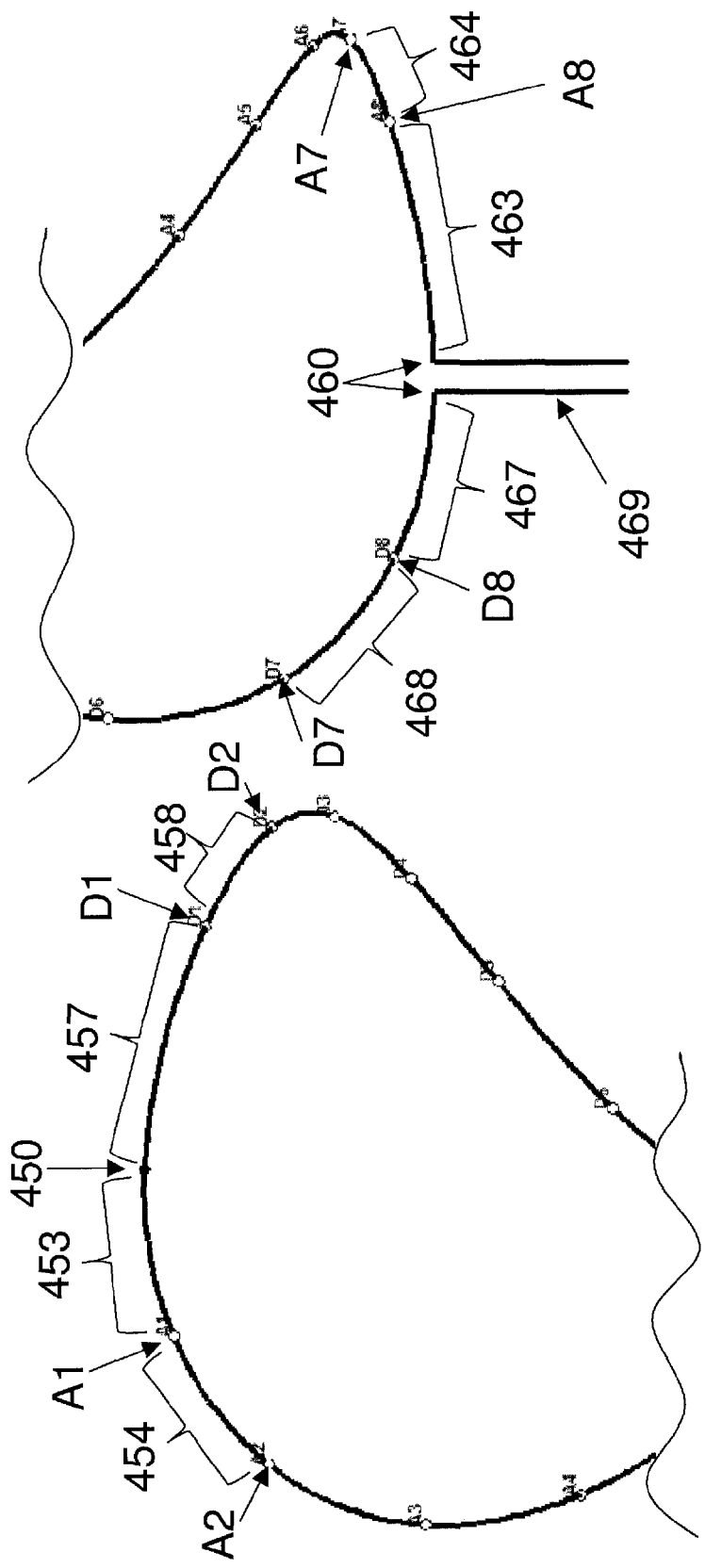
FIG. 26A shows the distal tip portion of the preshaped wire shown in FIG. 26
FIG. 26B shows the proximal portion of the preshaped wire shown in FIG. 26. The tip is labeled 450, proximal junction 460, and shaft 469. A portion of the electrodes are labeled as A1, A2, A7, A8, D1, D2, D7 and D8. Tip to electrode distances are labeled 453 and 457. Proximal junction to electrode distances are labeled 463 and 467. Inter-electrode distances along the spline are labeled 454, 458, 464 and 468.
Figure 27:
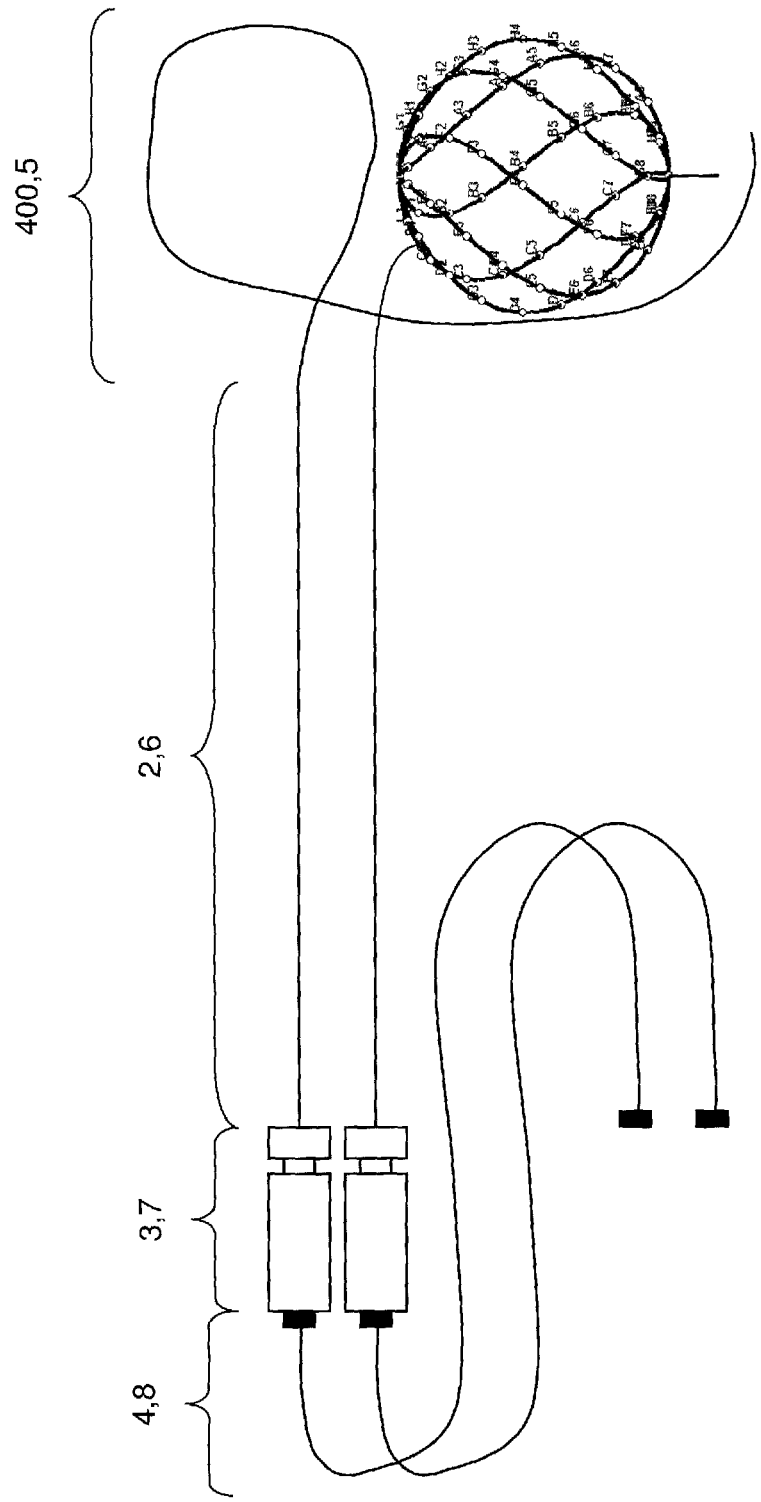
FIG. 27 shows the catheter system with the longitudinal spiral globe catheter 400 and RA-CS catheter 5 in relative position once deployed in the left atrium, right atrium and coronary sinus. The longitudinal spiral globe catheter that comprises a spiral globe portion 400, shaft portion 2, handle portion with an actuator 3, and a connecting cable portion 4.

FIGS. 25A-D and 26A-B further illustrate the electrode spacing discussed in the above section and illustrates the relationship between the preshaped metal-alloy wire and the electrodes. FIGS. 25A-D shows an 'odd' spline A and an 'even' spline D as being on one continuous preshaped wire. Referring to FIGS. 26A-B, the location of the continuous wire which will become the distal tip and the junction of spline A and spline D is labeled 450. Electrodes are labeled sequentially from the distal tip as A1 and A2, and D1 and D2. On the 'odd' spline A, the tip to A1 distance labeled 453 is the same as the distance between A1 and A2 labeled 454. All subsequent inter-electrode distances are equal to the distance between A1 and A2 including the distance between electrode A7 and A8 labeled 464. The distance between electrode A8 and the proximal inflection corner labeled 460 is one and one half times the inter-electrode distance between electrodes A7 and A8. On the 'even' spline D, the tip to D1 distance labeled 457 is one and one half times as the distance between D1 and D2 labeled 458. All subsequent inter-electrode distances are equal to the distance between D1 and D2 including the distance between electrode D7 and D8 labeled 468. The distance between electrode D8 and the proximal inflection corner labeled 460 is equal to the inter-electrode distance between electrodes D7 and D8. The proximal ends of the wires labeled 469 are used for physically connecting the splines to the shaft of the catheter.

The electrodes along the longitudinal spiral globe catheter may be spaced in an even and odd configuration as discussed above in reference to FIG. 22 globe catheter with improved electrode spacing to create a catheter with further improved electrode spacing. FIG. 23. is a model of a longitudinal spiral globe catheter with 8 spines, 8 electrodes per spline, a diameter of 50 mm, a rotation of one fourth pie radians, and evenly staggered electrodes on even and odd splines. In this model, the result has a the maximum inter-spline inter-electrode distance at the equator of the globe of 17.07 mm and intra-spline inter-electrode distance is 8.83 mm. If triangles are created from these electrodes, then the maximum ratio of the triangular edges between the splines to along the splines is 1.93. Hence, the longitudinal spiral globe catheter creates more uniform triangles across the surface of the globe than both the conventional globe catheter (ratio 3.04) and the globe catheter with improved electrode spacing (FIG. 22, ratio 2.48).

FIG. 24 shows an alternative longitudinal spiral globe catheter. This is a model of a longitudinal spiral globe catheter with 6 splines, 8 electrodes per spline, a diameter of 50 mm, a rotation of one third pie radians, and evenly staggered electrodes on even and odd splines. In this model, the result has a maximum inter-spline inter-electrode distance at the equator of the globe of 19.89 mm and intra-spline inter-electrode distance is 9.00 mm. If triangles are created from these electrodes, then the maximum ratio of the triangular edges between the splines to along the splines is 2.21. The six spline model has a reduced electrode number and may be simpler to manufacture than the eight spline model. The six spline model may be an adequate alternative to the eight spline model.

One advantage of the longitudinal spiral globe catheter is that the distribution of electrodes results in improved sampling of electrical signals compared to the conventional globe catheter. By having the splines cross the equator of the globe at an angle, the distance between splines is decreased around the equator of the globe. There is improved the spatial resolution of the catheter by reducing the inter-spline distances and subsequently the inter-spline inter-electrode distances. Overall, when the electrodes are reduced into a finite element model of triangles wherein the sensor elements form the vertices of the triangles, there is greater regularity of the triangles when compared to the conventional globe catheter.

A second advantage of the longitudinal spiral globe catheter is that it may maintain the relative position of electrodes better than the conventional globe catheter when being positioned in a chamber of the heart. The preshaped spiral of the spline allows for bending of spline along the curve of the spiral. This will allow for the longitudinal compression of the catheter without resulting in significant radial expansion such that the catheter will better accommodate the shape of the heart. Also when manipulating the catheter, if the catheter is rotated around its central axis and the distal tip of the catheter is in contact with an atrial wall resulting in decreased motion relative to the tip, then there would be a reduction in the diameter of the catheter around the equator since each of the splines would accommodate and increased number of turns around the globe. If rotation is then applied in the opposite direction, then there would be expansion of the globe around the equator which may allow for improved contact of the longitudinal spiral globe catheter with the chamber of the heart of interest.

The longitudinal spiral globe catheter may be used similar to the spiral globe catheter and be positioned in the left or right atrium and be used with or without the RA-CS catheter. When used positioned in the left atrium and the RA-CS catheter is used simultaneously, it may be considered as a catheter system.

In the preceding specification, the present invention has been described with reference to specific exemplary embodiments thereof. It, however, be evident that various modifications and changes may be made thereunto without departing from the broadest spirit and scope of the present invention. The specification and drawings are accordingly to be regarded as illustrative rather than restrictive sense.

It will be apparent to those skilled in the art that various modifications may be made in the present invention, without departing from the spirit or scope of the invention. Thus, it is intended that the present invention cover the modifications and variations of this invention provided they come within the scope of the appended claims and their equivalents.

What is claimed is:

1. A medical device, comprising:
   a handle portion comprising an actuator; and
   a catheter comprising a proximal end, a distal end and intermediate section therebetween, the catheter being coupled to the handle portion at the proximal end, the distal end of the catheter including a shape comprising a plurality of sequential loops around a central rotational axis, wherein the shape at the distal end of the catheter is a spiral globe shape, each of the plurality of sequential loops including a plurality of sensors,
   wherein the distal end comprises a shaft, the shaft comprising an actuator wire and one of a metal alloy strip or a metal alloy filament, wherein the actuator is configured to place tension on the actuator wire and the metal alloy strip or metal alloy filament acts as a compression element when tension is applied, such that the diameter of each of the sequential loops of the spiral globe is reduced to maintain the spiral globe shape,
   wherein the catheter further includes a tip portion that is distal to the shape comprising a plurality of sequential loops, and
   wherein the tip portion contains an electrode that serves as a unipolar reference.

2. The medical device of claim 1, wherein the plurality of sensors are one of electrodes for recording electrical signals from a heart or magnet sensors for use with a three-dimensional mapping system for recording a position of the catheter.

3. The medical device of claim 1, wherein the tip portion is distal to the spiral globe shape and is deflected at an angle of substantially 90 degrees with respect to a spiral globe surface of the spiral globe shape and oriented toward the center of the globe shape.

4. The medical device of claim 1, wherein the plurality of sequential loops have a constant rate of change of latitude versus longitude such that equidistant loops are formed.

5. The medical device of claim 1, wherein the distal end further includes a mitral valve region that is proximal to the plurality of sequential loops, the mitral valve region including a further plurality of sensors and being shaped to contact a circumference of a mitral valve of a heart.

6. The medical device of claim 1, wherein the distal end further includes preshaped curves to orient the central rotational axis toward a mitral valve relative to a inter-atrial septum and a shaft axis of the catheter.

7. The medical device of claim 1, wherein the proximal end of the catheter is coupled to the actuator such that a diameter of the plurality of sequential loops is controllable by the actuator.

8. The medical device of claim 1, wherein the plurality of sequential loops for a shape that comprises one of a spherical shape, a cylindrical shape, a rounded cylindrical shape, a conical shape, or a rounded conical shape.

9. The medical device of claim 1, wherein the plurality of sensors are positioned on the plurality of sequential loops such that the plurality of sensors form equal sized triangles.

10. The medical device of claim 9, wherein a ratio of a first distance between each of the plurality of sequential loops and a second distance between each sensor along a length of the shape is in a range from 1:1 to 3:1.

11. The medical device of claim 1, wherein a diameter of the shape is 40-70 mm.

12. A catheter system, comprising:
    a handle portion comprising an actuator;
    a first catheter configured to be deployed in a left atrium of a heart, the first catheter comprising a proximal end, a distal end and intermediate section therebetween, the distal end having a shape comprising a plurality of sequential loops around a central rotational axis, wherein the shape at the distal end of the first catheter is a spiral globe shape, each of the plurality of sequential loops including a plurality of electrodes,
    wherein the distal end comprises a shaft, the shaft comprising an actuator wire and one of a metal alloy strip or a metal alloy filament, wherein the actuator is configured to place tension on the actuator wire and the metal alloy strip or metal alloy filament acts as a compression element when tension is applied, such that the diameter of each of the sequential loops of the spiral globe is reduced to maintain the spiral globe shape,
    wherein the first catheter further includes a tip portion that is distal to the shape comprising a plurality of sequential loops, and
    wherein the tip portion contains an electrode that serves as a unipolar reference;
    a second catheter configured to be deployed in a right atrium and a coronary sinus of the heart, the second catheter comprising a proximal end, a distal end and intermediate section therebetween, the distal end comprising a second plurality of electrodes; and
    a processing unit electrically coupled to the plurality of electrodes of the first catheter and the second plurality of electrodes of the second catheter, the processing unit receiving signals from the plurality of electrodes and second plurality of electrodes.

13. The catheter system of claim 12, wherein the processing unit records a plurality of simultaneous electrograms for the left atrium, the right atrium and the coronary sinus based on the signals.

14. The catheter system of claim 12, wherein the first catheter further includes sensors generating sensor signals, the processing unit receiving the sensor signals to generate a position of the first catheter relative to a three-dimensional map of the heart.

15. The catheter system of claim 14, wherein the sensors are magnetic sensors.

16. The catheter system of claim 12, further comprising:
    a third catheter configured to be deployed to either the right or left atrium, the third catheter comprising a proximal end, a distal end and intermediate section therebetween, wherein the distal end includes a sensor to record sensor signals in the atrium in which the third catheter is deployed, the distal end further comprising an ablation element.

17. A method, comprising:
    introducing a catheter into an atrium of a heart, the catheter comprising a proximal end, a distal end and intermediate section therebetween;

deploying the catheter in the atrium, wherein the distal end of the catheter being coupled to a handle portion at the proximal end has a shape comprising a plurality of sequential loops around a central rotational axis, wherein the shape at the distal end of the catheter is a spiral globe shape, each of the plurality of sequential loops including a plurality of electrodes, wherein at least a portion of the plurality of electrodes are in close proximity to a wall of the atrium, wherein the distal end comprises a shaft, the shaft comprising an actuator wire and one of a metal alloy strip or a metal alloy filament, wherein an actuator is configured to place tension on the actuator wire and the metal alloy strip or metal alloy filament acts as a compression element when tension is applied, such that the diameter of each of the sequential loops of the spiral globe is reduced to maintain the spiral globe shape, wherein the catheter further includes a tip portion that is distal to the shape comprising a plurality of sequential loops, and wherein the tip portion contains an electrode that serves as a unipolar reference;

collecting electrical signals from the atrium via the plurality of electrodes in close proximity to the wall of the atrium; and generating an electrogram based on the electrical signals.

18. The method of claim 17, further comprising:

collecting further signals from further sensors of the catheter;

determining a location of the catheter based on the further signals; and mapping the location of the catheter relative to a three-dimensional map of the atrium.

19. The method of claim 17, further comprising:

introducing a second catheter into another atrium of the heart, the second catheter comprising a proximal end, a distal end and intermediate section therebetween, the distal end comprising a second plurality of electrodes;

deploying the catheter in the another atrium;

collecting electrical signals from the another atrium via the second plurality of electrodes; and simultaneously with generating the electrogram, generating a second electrogram based on the electrical signals collected from the second plurality of electrodes.

20. The method of claim 17, wherein the introducing of the second catheter includes introducing the second catheter into a coronary sinus of the heart and the deploying includes deploying the second catheter into the coronary sinus, wherein at least a portion of the second plurality of electrodes are deployed in the coronary sinus, the method further comprising:

collecting electrical signals from the coronary sinus via the at least a portion of the second plurality of electrodes; and simultaneously with generating the electrogram and the second electrogram, generating a third electrogram based on the electrical signals collected from the at least a portion of the second plurality of electrodes.

21. The method of claim 17, wherein tip portion is distal to the spiral globe shape and the deploying includes orienting the tip portion central to a first loop of the spiral globe shape so that the tip is protected from contact with a wall of the atrium.

22. A medical device, comprising:

a handle portion comprising an actuator; and a catheter comprising a proximal end, a distal end and intermediate section therebetween, the catheter being coupled to the handle portion at the proximal end, the distal end of the catheter being split into two tips, each tip having a shape comprising a plurality of sequential loops around a central rotational axis, wherein the shape at each tip is a spiral globe shape, wherein the plurality of sequential loops of a first tip are opposed to the plurality of sequential loops of a second tip, each of the plurality of sequential loops including a plurality of sensors, wherein the each of the two tips comprises a shaft, the shaft comprising an actuator wire and one of a metal alloy strip or a metal alloy filament, wherein the actuator is configured to place tension on the actuator wire and the metal alloy strip or metal alloy filament acts as a compression element when tension is applied, such that the diameter of each of the sequential loops of the spiral globes is reduced to maintain the spiral globe shape, wherein the catheter further includes a tip portion that is distal to the shape comprising a plurality of sequential loops, and wherein the tip portion contains an electrode that serves as a unipolar reference.

23. The medical device of claim 22, wherein the shape of the first tip and the shape of the second tip are symmetrical.

24. The medical device of claim 22, wherein the shape of the first tip and the shape o the second tip are asymmetrical.

25. The medical device of claim 22, wherein the proximal end of the catheter is coupled to the actuator such that such that a diameter of the plurality of sequential loops of each tip is controllable by the actuator.

26. The medical device of claim 22, further comprising a connector that connects a distal end of the first tip to a distal end of the second tip.

\* \* \* \* \*